United States Patent
Edwards et al.

(10) Patent No.: US 6,749,607 B2
(45) Date of Patent: *Jun. 15, 2004

(54) APPARATUS TO TREAT ESOPHAGEAL SPHINCTERS

(75) Inventors: Stuart D Edwards, Salinas, CA (US); David S Utley, Redwood City, CA (US)

(73) Assignee: Curon Medical, Inc., Fremont, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/971,085

(22) Filed: Oct. 4, 2001

(65) Prior Publication Data

US 2002/0123748 A1 Sep. 5, 2002

Related U.S. Application Data

(63) Continuation of application No. 09/036,092, filed on Mar. 6, 1998, now abandoned.

(51) Int. Cl.[7] .............................................. A61B 18/18
(52) U.S. Cl. .......................................... 606/41; 607/101
(58) Field of Search ............................ 606/41, 42, 45, 606/48–50; 607/101, 102, 115, 116, 133, 122

(56) References Cited

U.S. PATENT DOCUMENTS

| | | |
|---|---|---|
| 1,798,902 A | 3/1931 | Raney |
| 3,517,128 A | 6/1970 | Hines |
| 3,901,241 A | 8/1975 | Allen, Jr. |
| 4,011,872 A | 3/1977 | Komiya |
| 4,196,724 A | 4/1980 | Wirt et al. |
| 4,411,266 A | 10/1983 | Cosman |
| 4,423,812 A | 1/1984 | Sato |
| 4,532,924 A | 8/1985 | Auth et al. |
| 4,565,200 A | 1/1986 | Cosman |
| 4,705,041 A | 11/1987 | Kim |

(List continued on next page.)

FOREIGN PATENT DOCUMENTS

| | | | |
|---|---|---|---|
| DE | 43 03 882 A | 2/1995 | |
| DE | 38 38 840 A | 2/1997 | |
| EP | 0 139 607 A1 | 5/1985 | |
| EP | 0 608 609 A2 | 8/1994 | |
| WO | WO 91/01773 | 2/1991 | ......... A61M/29/00 |
| WO | 92/10142 | 6/1992 | |
| WO | 93/08755 | 5/1993 | |
| WO | 94/10925 | 5/1994 | |
| WO | 94/26178 | 11/1994 | |
| WO | 95/18575 | 7/1995 | |

(List continued on next page.)

OTHER PUBLICATIONS

Castell, D. O. "Gastroesophageal Reflux Disease: Current Strategies for Patient Management." *Arch Fam Med.* 5(4): 221–7.

(List continued on next page.)

*Primary Examiner*—Michael Peffley
(74) *Attorney, Agent, or Firm*—Ryan Kromholz & Manion, S.C.

(57) ABSTRACT

A sphincter treatment apparatus has an introducer means including a distal portion means. An expandable device means includes a plurality of arm means. Each arm means of the plurality has a distal section means and a proximal section means. Each of distal sections means of the arm means are coupled and each of the proximal sections means of the arm means are coupled to the introducer means distal portion means. The expandable device means is configured to at least partially dilate a sphincter in a deployed state. An energy delivery device means is introduceable from the introducer means into a selected site of the sphincter. The energy delivery device means is configured to deliver sufficient energy to reduce a frequency of relaxation of the sphincter.

90 Claims, 23 Drawing Sheets

U.S. PATENT DOCUMENTS

| | | |
|---|---|---|
| 4,901,737 A | 2/1990 | Toone |
| 4,906,203 A | 3/1990 | Margrave et al. |
| 4,907,589 A | 3/1990 | Cosman |
| 4,943,290 A | 7/1990 | Rexroth et al. |
| 4,947,842 A | 8/1990 | Marchosky et al. |
| 4,966,597 A | 10/1990 | Cosman |
| 4,976,711 A | 12/1990 | Parins et al. |
| 5,035,696 A | 7/1991 | Rydell |
| 5,046,512 A | 9/1991 | Murchie |
| 5,057,107 A | 10/1991 | Parins et al. |
| 5,078,717 A | 1/1992 | Parins et al. |
| 5,083,565 A | 1/1992 | Parins |
| 5,088,979 A | 2/1992 | Filipi et al. |
| 5,094,233 A | 3/1992 | Brennan |
| 5,100,423 A | 3/1992 | Fearnot |
| 5,122,137 A | 6/1992 | Lennox |
| 5,125,928 A | 6/1992 | Parins et al. |
| 5,156,151 A * | 10/1992 | Imran ............... 600/375 |
| 5,190,541 A | 3/1993 | Abele et al. |
| 5,197,963 A | 3/1993 | Parins |
| 5,197,964 A | 3/1993 | Parins |
| 5,205,287 A | 4/1993 | Erbel et al. |
| 5,215,103 A | 6/1993 | Desai |
| 5,254,126 A | 10/1993 | Filipi et al. |
| 5,256,138 A | 10/1993 | Burek et al. |
| 5,257,451 A | 11/1993 | Edwards et al. |
| 5,263,493 A * | 11/1993 | Avitall ............... 600/374 |
| 5,275,162 A | 1/1994 | Edwards et al. |
| 5,275,608 A | 1/1994 | Forman et al. |
| 5,277,201 A | 1/1994 | Stern |
| 5,281,216 A | 1/1994 | Klicek |
| 5,281,217 A | 1/1994 | Edwards et al. |
| 5,281,218 A | 1/1994 | Imran |
| 5,290,286 A | 3/1994 | Parins |
| 5,293,869 A | 3/1994 | Edwards et al. |
| 5,309,910 A | 5/1994 | Edwards et al. |
| 5,313,943 A * | 5/1994 | Houser et al. ........... 600/374 |
| 5,314,466 A | 5/1994 | Stern et al. |
| 5,316,020 A | 5/1994 | Truffer |
| 5,328,467 A | 7/1994 | Edwards et al. |
| 5,334,196 A | 8/1994 | Scott et al. |
| 5,345,936 A * | 9/1994 | Pomeranz et al. ........ 600/374 |
| 5,348,554 A | 9/1994 | Imran et al. |
| 5,363,861 A | 11/1994 | Edwards et al. |
| 5,365,926 A | 11/1994 | Desai |
| 5,365,945 A | 11/1994 | Halstrom |
| 5,366,490 A | 11/1994 | Edwards et al. |
| 5,368,557 A | 11/1994 | Nita et al. |
| 5,368,592 A | 11/1994 | Stern et al. |
| 5,370,675 A * | 12/1994 | Edwards et al. ........ 607/101 |
| 5,370,678 A | 12/1994 | Edwards et al. |
| 5,383,876 A | 1/1995 | Nardella |
| 5,383,917 A | 1/1995 | Desai |
| 5,385,544 A | 1/1995 | Edwards et al. |
| 5,397,339 A | 3/1995 | Desai |
| 5,398,683 A | 3/1995 | Edwards et al. |
| 5,401,272 A | 3/1995 | Perkins |
| 5,403,311 A | 4/1995 | Abele et al. |
| 5,409,453 A | 4/1995 | Lundquist et al. |
| 5,411,025 A * | 5/1995 | Webster, Jr. ............. 600/374 |
| 5,421,819 A | 6/1995 | Edwards et al. |
| 5,423,808 A | 6/1995 | Edwards et al. |
| 5,423,811 A | 6/1995 | Imran et al. |
| 5,423,812 A | 6/1995 | Ellman et al. |
| 5,433,739 A | 7/1995 | Sluijter et al. |
| 5,435,805 A | 7/1995 | Edwards et al. |
| 5,441,499 A | 8/1995 | Fritzsch |
| 5,454,782 A | 10/1995 | Perkins |
| 5,456,662 A | 10/1995 | Edwards et al. |
| 5,456,682 A | 10/1995 | Edwards et al. |
| 5,458,596 A | 10/1995 | Lax et al. |
| 5,458,597 A | 10/1995 | Edwards et al. |
| 5,465,717 A | 11/1995 | Imran et al. |
| 5,470,308 A | 11/1995 | Edwards et al. |
| 5,471,982 A | 12/1995 | Edwards et al. |
| 5,472,441 A | 12/1995 | Edwards et al. |
| 5,484,400 A | 1/1996 | Edwards et al. |
| 5,486,161 A | 1/1996 | Lax et al. |
| 5,490,984 A | 2/1996 | Freed |
| 5,505,728 A | 4/1996 | Ellman et al. |
| 5,505,730 A | 4/1996 | Edwards |
| 5,507,743 A | 4/1996 | Edwards et al. |
| 5,509,419 A | 4/1996 | Edwards et al. |
| 5,514,130 A | 5/1996 | Baker |
| 5,514,131 A | 5/1996 | Edwards et al. |
| 5,520,684 A | 5/1996 | Imran |
| 5,531,676 A | 7/1996 | Edwards et al. |
| 5,531,677 A | 7/1996 | Lundquist et al. |
| 5,536,240 A | 7/1996 | Edwards et al. |
| 5,536,267 A | 7/1996 | Edwards et al. |
| 5,540,655 A | 7/1996 | Edwards et al. |
| 5,542,915 A | 8/1996 | Edwards et al. |
| 5,542,916 A | 8/1996 | Hirsch et al. |
| 5,545,161 A | 8/1996 | Imran |
| 5,545,171 A | 8/1996 | Sharkey et al. |
| 5,545,193 A | 8/1996 | Fleischman et al. |
| 5,545,434 A | 8/1996 | Huarng |
| 5,549,108 A | 8/1996 | Edwards et al. |
| 5,549,644 A | 8/1996 | Lundquist et al. |
| 5,554,110 A | 9/1996 | Edwards et al. |
| 5,556,377 A | 9/1996 | Rosen et al. |
| 5,558,672 A | 9/1996 | Edwards et al. |
| 5,558,673 A | 9/1996 | Edwards et al. |
| 5,571,116 A | 11/1996 | Bolanos et al. |
| 5,578,007 A * | 11/1996 | Imran ............... 604/95 |
| 5,599,345 A | 2/1997 | Edwards et al. |
| 5,609,151 A | 3/1997 | Mulier et al. |
| 5,624,439 A | 4/1997 | Edwards et al. |
| 5,676,674 A | 10/1997 | Bolanos et al. |
| 5,688,490 A | 11/1997 | Tournier et al. |
| 5,702,438 A * | 12/1997 | Avitall ............... 607/122 |
| 5,709,224 A * | 1/1998 | Behl et al. ............. 128/898 |
| 6,073,052 A | 6/2000 | Zelickson et al. |
| 6,254,598 B1 * | 7/2001 | Edwards et al. ........ 606/41 |
| 6,440,128 B1 * | 8/2002 | Edwards et al. ........ 606/41 |
| 6,464,697 B1 * | 10/2002 | Edwards et al. ........ 606/41 |

FOREIGN PATENT DOCUMENTS

| | | | |
|---|---|---|---|
| WO | 95/19142 | 7/1995 | |
| WO | 95/25472 | 9/1995 | |
| WO | 96/29946 | 10/1996 | |
| WO | WO 97/06857 | 2/1997 | ........... A61N/5/06 |

OTHER PUBLICATIONS

Dallemagne, B., et al. "Laparoscopic Nissen Fundoplication: Preliminary Report." *Surgical Laparoscopy & Endoscopy.* 1991. 1(3): 138–43.

Hinder, R. A., et al. "The Technique of Laparoscopic Nissen Fundoplication." *Surgical Laparoscopy & Endoscopy.* 1992. 1992. 2(3): 265–272.

Karlstrom, L. H. et al. "Ectopic jejunal pacemakers and enterogastric reflux after Roux gastrectomy: Effect of intestinal pacing." *Surgery.* 1989. 106(3): 486–495.

Kelly, K. A., et al., "Duodenal–gastric reflux and slowed gastric emptying by electrical pacing of the canine duodenal pacesetter potential." *Gastroenterology.* 1977. 72(3):429–33.

Reynolds, J. C. "Influence of pathophysiology, severity, and cost on the medical management of gastroesophageal reflux disease." *Am J Health–Syst Pharm*. 53 (22 Suppl 3): S5–12.

Urschel, J. D. "Complications of Antireflux Surgery." *Am J Surg*. 1993. 166(1): 68–70.

Kaneko, et al., *Physiological Laryngeal Pacemaker*, May 1985, Trans Am Soc Artif Intern Organs, vol. XXXI, pp. 293–296.

Mugica, et al., *Direct Diaphragm Stimulation*, Jan. 1987, PACE, vol. 10, pp. 252–256.

Mugica, et al., *Neurostimulation: An Overview*, Chapter 21, *Preliminary Test of a Muscular Diaphragm Pacing System on Human Patients*, 1985, pp. 263–279.

Nochomovitz, et al., *Electrical Activation of the Diaphragm*, Jun. 1988, Clinics in Chest Medicine, vol. 9, No. 2, pp. 349–358.

Prior, et al., *Treatment of Menorrhagia by Radiofrequency Heating*, 1991, Int. J. Hyperthermia, vol. 7, pp. 213–220.

Rice, et al., *Endoscopic Paranasal Sinus Surgery*, Chapters 5, *Functional Endoscopic Paranasal Sinus Surgery, The Technique of Messerklinger*, Raven Press, 1988, pp. 75–104.

Rice, et al., *Endoscopic Paranasal Sinus Surgery*, Chapters 6, *Total Endoscopic Sphenoethmoidectomy, The Technique of Wigand*, Raven Press, 1988, pp. 105–125.

* cited by examiner

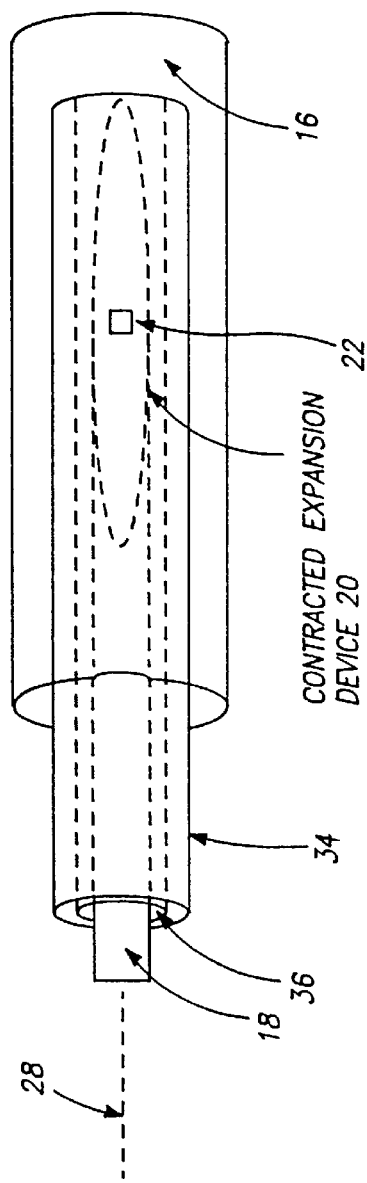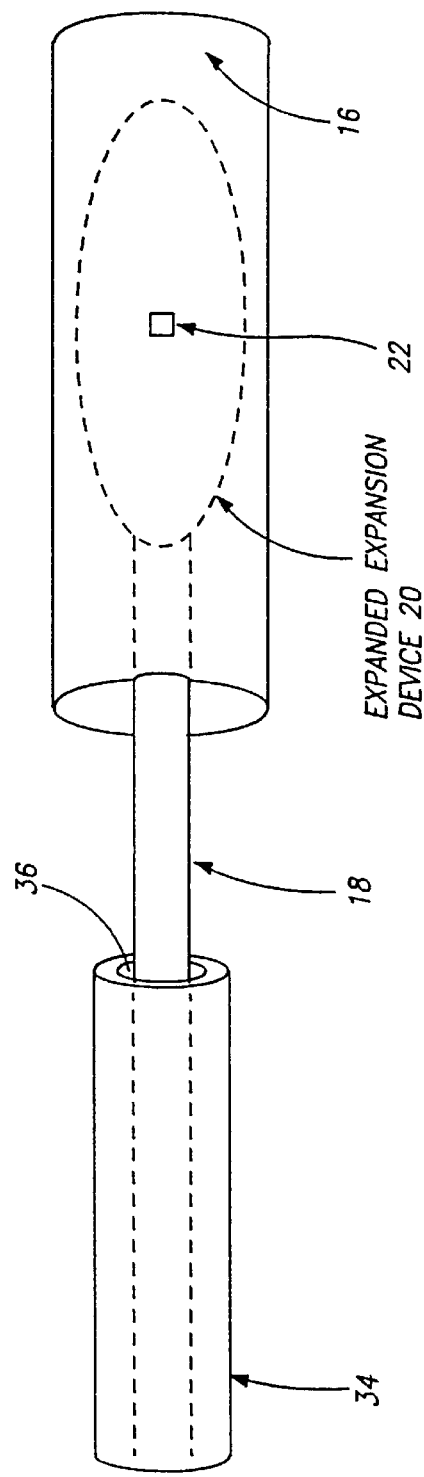
FIG.-3A
FIG.-3B

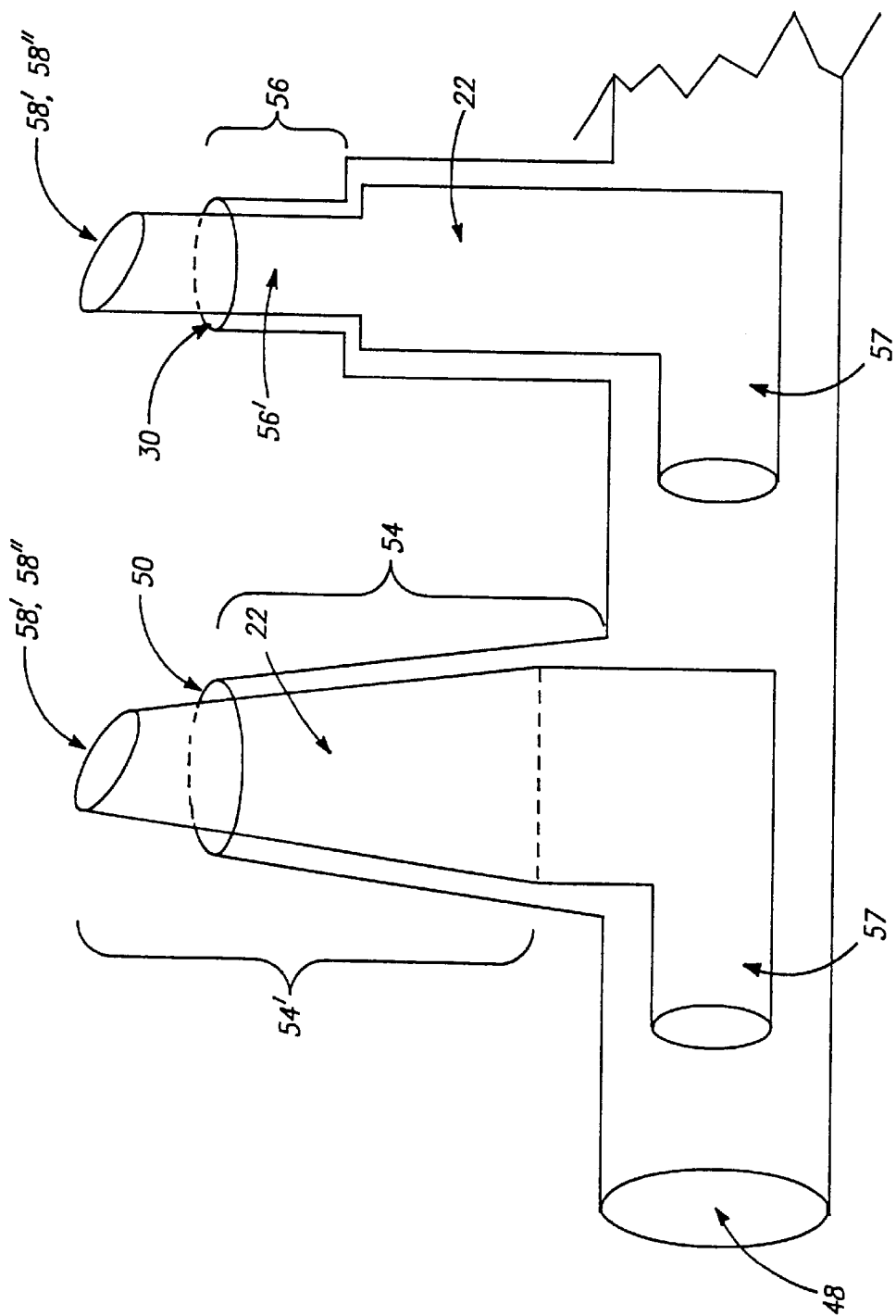

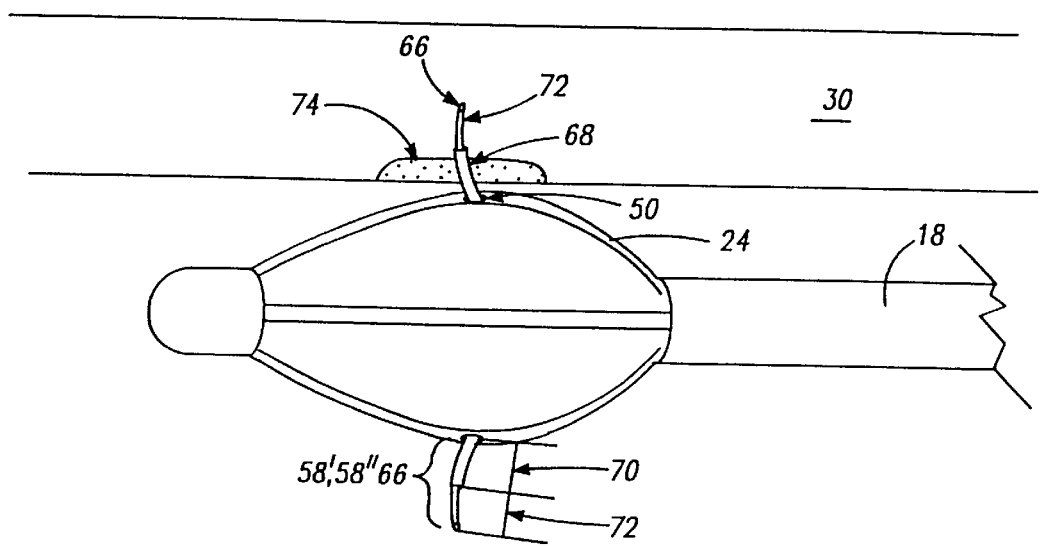
FIG.—11

FIG.−16

APPARATUS TO TREAT ESOPHAGEAL SPHINCTERS

CROSS-RELATED APPLICATIONS

This application is a continuation of U.S. patent application Ser. No. 09/036,092, filed Mar. 6, 1998 now abandoned.

FIELD OF THE INVENTION

This invention relates generally to an apparatus to treat sphincters, and more particularly to an apparatus to treat esophageal sphincters.

DESCRIPTION OF RELATED ART

Gastroesophageal reflux disease (GERD) is a common gastroesophageal disorder in which the stomach contents are ejected into the lower esophagus due to a dysfunction of the lower esophageal sphincter (LES). These contents are highly acidic and potentially injurious to the esophagus resulting in a number of possible complications of varying medical severity. The reported incidence of GERD in the U.S. is as high as 10% of the population (Castell D O; Johnston B T: *Gastroesophageal Reflux Disease: Current Strategies For Patient Management*. Arch Fam Med, 5(4):221–7; (1996 April)).

Acute symptoms of GERD include heartburn, pulmonary disorders and chest pain. On a chronic basis, GERD subjects the esophagus to ulcer formation, or esophagitis and may result in more severe complications including esophageal obstruction, significant blood loss and perforation of the esophagus. Severe esophageal ulcerations occur in 20–30% of patients over age 65. Moreover, GERD causes adenocarcinoma, or cancer of the esophagus, which is increasing in incidence faster than any other cancer (Reynolds J C: *Influence Of Pathophysiology, Severity, And Cost On The Medical Management Of Gastroesophageal Reflux Disease*. Am J Health Syst Pharm, 53(22 Suppl 3):S5–12 (Nov. 15, 1996)).

Current drug therapy for GERD includes histamine receptor blockers which reduce stomach acid secretion and other drugs which may completely block stomach acid. However, while pharmacologic agents may provide short term relief, they do not address the underlying cause of LES dysfunction.

Invasive procedures requiring percutaneous introduction of instrumentation into the abdomen exist for the surgical correction of GERD. One such procedure, Nissen fundoplication, involves constructing a new "valve" to support the LES by wrapping the gastric fundus around the lower esophagus. Although the operation has a high rate of success, it is an open abdominal procedure with the usual risks of abdominal surgery including: postoperative infection, herniation at the operative site, internal hemorrhage and perforation of the esophagus or of the cardia. In fact, a recent 10 year, 344 patient study reported the morbidity rate for this procedure to be 17% and mortality 1% (Urschel, J D: *Complications Of Antireflux Surgery*, Am J Surg 166(1): 68–70; (1993 July)). This rate of complication drives up both the medical cost and convalescence period for the procedure and may exclude portions of certain patient populations (e.g., the elderly and immuno-compromised).

Efforts to perform Nissen fundoplication by less invasive techniques have resulted in the development of laparoscopic Nissen fundoplication. Laparoscopic Nissen fundoplication, reported by Dallemagne et al. Surgical Laparoscopy and Endoscopy, Vol. 1, No. 3, (1991), pp. 138–43 and by Hindler et al. Surgical Laparoscopy and Endoscopy, Vol. 2, No. 3, (1992), pp. 265–272, involves essentially the same steps as Nissen fundoplication with the exception that surgical manipulation is performed through a plurality of surgical cannula introduced using trocars inserted at various positions in the abdomen.

Another attempt to perform fundoplication by a less invasive technique is reported in U.S. Pat. No. 5,088,979. In this procedure, an invagination device containing a plurality of needles is inserted transorally into the esophagus with the needles in a retracted position. The needles are extended to engage the esophagus and fold the attached esophagus beyond the gastroesophageal junction. A remotely operated stapling device, introduced percutaneously through an operating channel in the stomach wall, is actuated to fasten the invaginated gastroesophageal junction to the surrounding involuted stomach wall.

Yet another attempt to perform fundoplication by a less invasive technique is reported in U.S. Pat. No. 5,676,674. In this procedure, invagination is done by a jaw-like device and fastening of the invaginated gastroesophageal junction to the fundus of the stomach is done via a transoral approach using a remotely operated fastening device, eliminating the need for an abdominal incision. However, this procedure is still traumatic to the LES and presents the postoperative risks of gastroesophageal leaks, infection and foreign body reaction, the latter two sequela resulting when foreign materials such as surgical staples are implanted in the body.

While the methods reported above are less invasive than an open Nissen fundoplication, some still involve making an incision into the abdomen and hence the increased morbidity and mortality risks and convalescence period associated with abdominal surgery. Others incur the increased risk of infection associated with placing foreign materials into the body. All involve trauma to LES and the risk of leaks developing at the newly created gastroesophageal junction.

Besides the LES, there are other sphincters in the body which if not functionally properly can cause disease states or otherwise adversely affect the lifestyle of the patient. Reduced muscle tone or otherwise aberrant relaxation of sphincters can result in a laxity of tightness disease states including, but not limited to, urinary incontinence.

There is a need to provide an apparatus to treat a sphincter and reduce a frequency of sphincter relaxation. Another need exists for an apparatus to create controlled cell necrosis in a sphincter tissue underlying a sphincter mucosal layer. Yet another need exists for an apparatus to create controlled cell necrosis in a sphincter and minimize injury to a mucosal layer of the sphincter. There is another need for an apparatus to controllably produce a lesion in a sphincter without creating a permanent impairment of the sphincter's ability to achieve a physiologically normal state of closure. Still a further need exists for an apparatus to create a tightening of a sphincter without permanently damaging anatomical structures near the sphincter. There is still another need for an apparatus to create controlled cell necrosis in a lower esophageal sphincter to reduce a frequency of reflux of stomach contents into an esophagus.

SUMMARY OF THE INVENTION

Accordingly, an object of the present invention is to provide an apparatus that reduces a frequency of sphincter relaxation.

Another object of the invention is to provide an apparatus to create controlled cell necrosis in a sphincter tissue underlying a sphincter mucosal layer.

Yet another object of the invention is to provide an apparatus to create controlled cell necrosis in a sphincter and minimize injury to a mucosal layer of the sphincter.

A further object of the invention is to provide an apparatus to controllably produce a lesion in a sphincter without creating a permanent impairment of the sphincter's ability to achieve a physiologically normal state of closure.

Still another object of the invention is to provide an apparatus to create a tightening of a sphincter without permanently damaging anatomical structures near the sphincter.

Another object of the invention is to provide an apparatus to create controlled cell necrosis in a lower esophageal sphincter to reduce a frequency of reflux of stomach contents into an esophagus.

These and other objects of the invention are provided in a sphincter treatment apparatus within an introducer means including a distal portion means. An expandable device means includes a plurality of arm means. Each arm means has a distal section means and a proximal section means. Each of the distal section means of the arm means are coupled and each of the proximal section means of the arm means are coupled to the introducer means distal portion means. The expandable device means is configured to at least partially dilate a sphincter in a deployed state. An energy delivery device means is introduceable from the introducer means into a selected site of the sphincter. The energy delivery device means is configured to deliver sufficient energy to reduce a frequency of relaxation of the sphincter.

In another embodiment, an expandable device means is coupled to an introducer distal portion means. The expandable device means includes a first arm means with a proximal and distal section means and a second arm means with proximal and distal section means. The first and second arm distal portion means are coupled. The expandable device means is configured to at least partially dilate a sphincter in a deployed state. An energy delivery device means is coupled to the expandable device means. The energy delivery device means is configured to deliver sufficient energy to reduce a frequency of relaxation of the sphincter while minimizing cell necrosis of a mucosal layer of the sphincter.

BRIEF DESCRIPTION OF THE DRAWINGS

FIGS. 3a and 3b depicts a lateral view of an embodiment of the invention that illustrates the use of a sheath to introduce and deploy the expansion device.

FIG. 7A is a cross-sectional view of a section of a basket arm and an energy delivery device illustrating stepped and tapered sections in the basket arm apertures and energy delivery device.

FIG. 11 is a lateral view illustrating the use of an insulation layer on the needle electrode to protect an area of tissue from RF energy.

DETAILED DESCRIPTION

Figure 1:
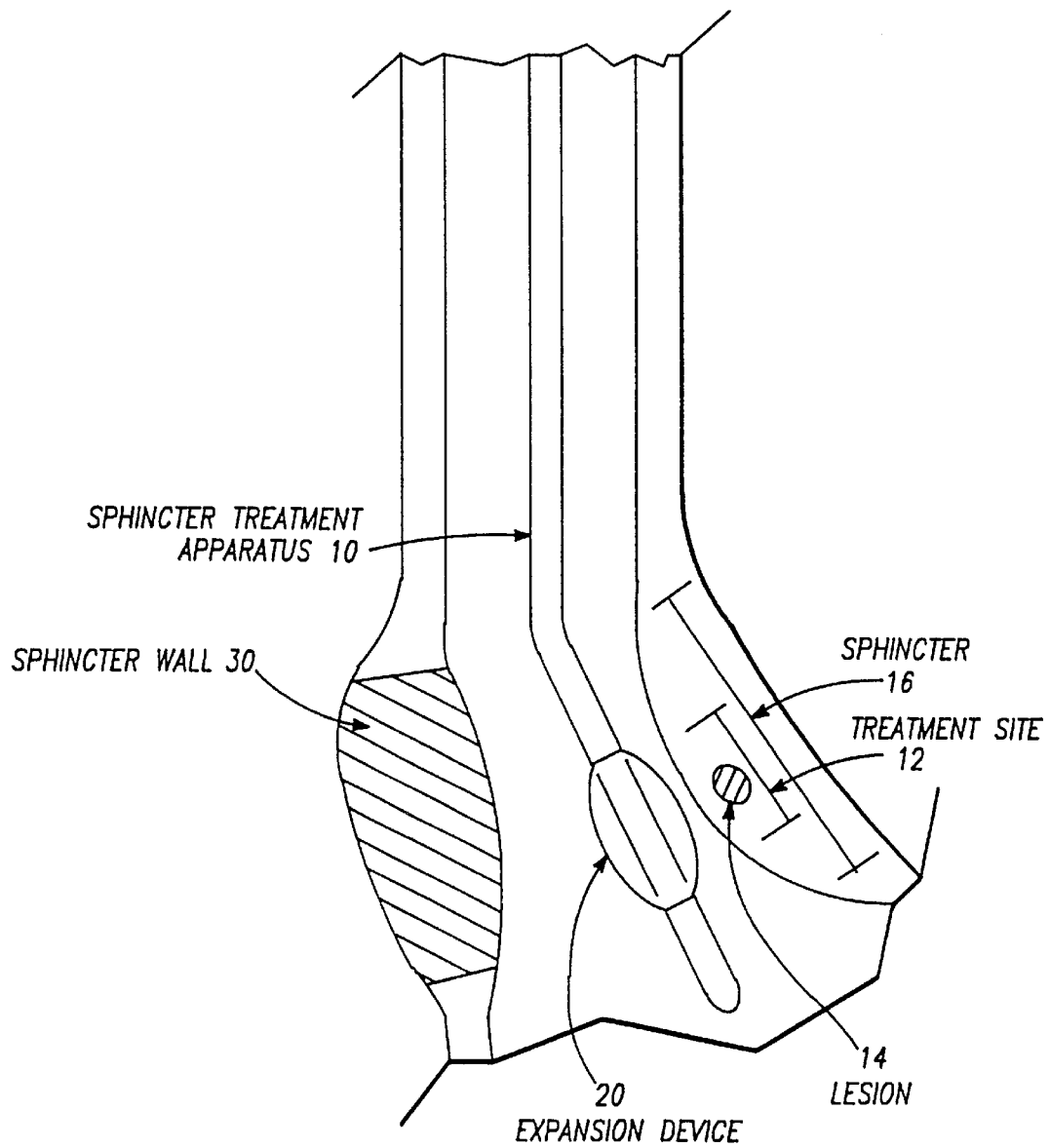
FIG. 1 is an illustrated lateral view of the upper GI tract depicting the position of the sphincter treatment apparatus of the present invention in the lower esophageal sphincter.
Figure 2:
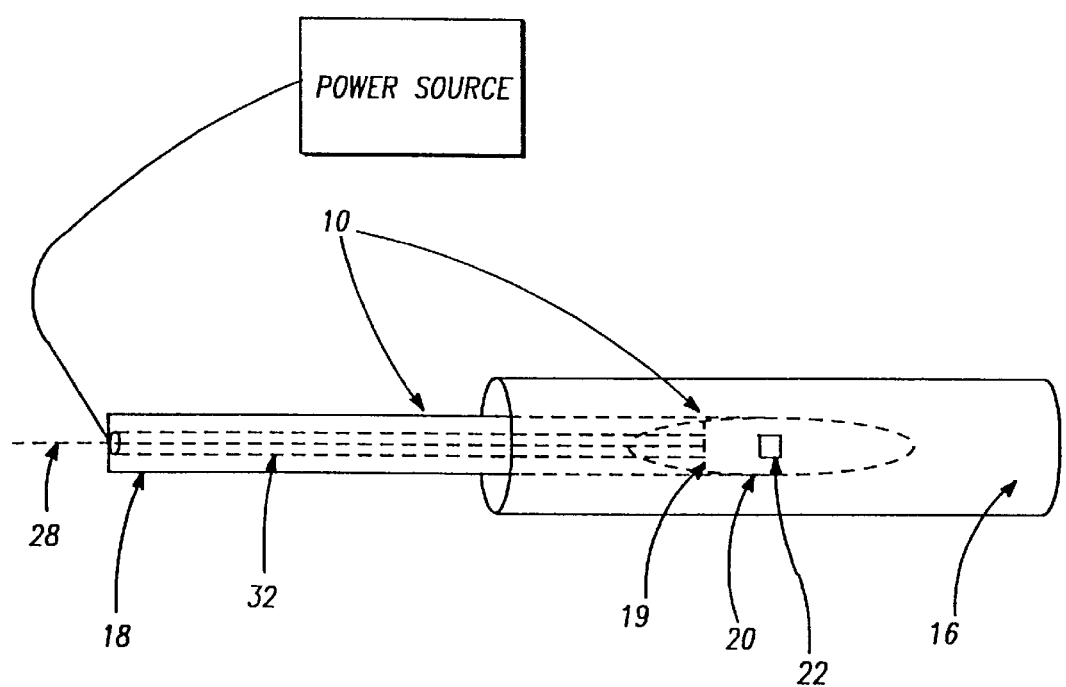
FIG. 2 is a lateral view of the present invention illustrating the introducer, expansion device and energy delivery device.

Referring to FIGS. 1 and 2, one embodiment of a sphincter treatment apparatus 10 delivers energy to a treatment site 12 to produce lesions 14 in a sphincter 16, such as the lower esophageal sphincter (LES). In this embodiment, sphincter treatment apparatus 10 comprises a flexible elongate shaft 18, also called introducer 18, coupled to an expansion device 20, in turn coupled with one or more energy delivery devices 22. Introducer 18 has a distal extremity also called introducer end 19. Energy delivery devices 22 are configured to be coupled to a power source.

Expansion device 20 comprises a plurality of arms 24, with proximal and distal arms ends 25 and 26. Proximal arm ends 25 are coupled to introducer end 19. Expansion device 20 has a central longitudinal axis 28 and is moveable between contracted and expanded/deployed states substantially there along. Expansion device 20 is configured to be positionable in a sphincter 16 (such as the LES) or adjacent anatomical structure (such as the cardia of the stomach) and is further configured to partially dilate sphincter 16 when in the deployed state. Energy delivery devices 22 are configured to be introduceable from introducer 18 and to contact and/or penetrate a targeted treatment site 12 in a sphincter wall 30 or adjoining anatomical structure. They are further configured to deliver energy to treatment site 12.

Referring now to FIG. 2, introducer 18 is configured to be coupled to expansion device 20 and has sufficient length to position expansion device 20 in the LES and/or stomach using a transoral approach. Typical lengths for introducer 18 include a range of 40–180 cm. Introducer 18 may be circular or oval in cross section. Also, introducer 18 may be flexible, articulated, coil-reinforced, or steerable, or any combination thereof. Suitable materials for introducer 18 include polyethylenes, polyurethanes, silicones and other biocompatible polymers known to those skilled in the art. Introducer 18 may also be coated with a lubricious coating as is well known to those skilled in the art.

Introducer 18 may have one or more lumens 32, that extend the full length of introducer 18, or only a portion thereof. Lumens 32 may be used as paths for the delivery of fluids and gases, as well as providing channels for cables, catheters, guide wires, pull wires, insulated wires, and optical fibers.

In another embodiment of the invention depicted in FIG. 3, an introduction member 34, also called a sheath 34, is used to introduce sphincter treatment apparatus 10 into the LES. Sheath 34 can also function as a sheath for expansion device 20 to keep it in a nondeployed or contracted state during introduction into the LES. To facilitate this function, sheath 34 contains a sheath lumen 36 of sufficient inner diameter to allow free movement of sphincter treatment apparatus 10 within sheath lumen 36. Sheath 34, sheath lumen 36 and sphincter treatment apparatus 10 are configured to allow expansion device 20 to go from a contracted state to an expanded state and vice versa by either i) the retraction or advancement of sheath 34, or ii) the advancement or withdrawal of sphincter treatment apparatus 10. Sheath 34 may be flexible, articulated, coil-reinforced or steerable, or any combination thereof. Suitable materials for sheath 34 include polyethylenes, polyurethanes, silicones, polytetrafluoroethylenes and other biocompatible polymers known to those skilled in the art. Typical diameters for sheath lumen 36 include 0.1 to 2 inches, while typical lengths include 40–180 cms.

Figure 4:
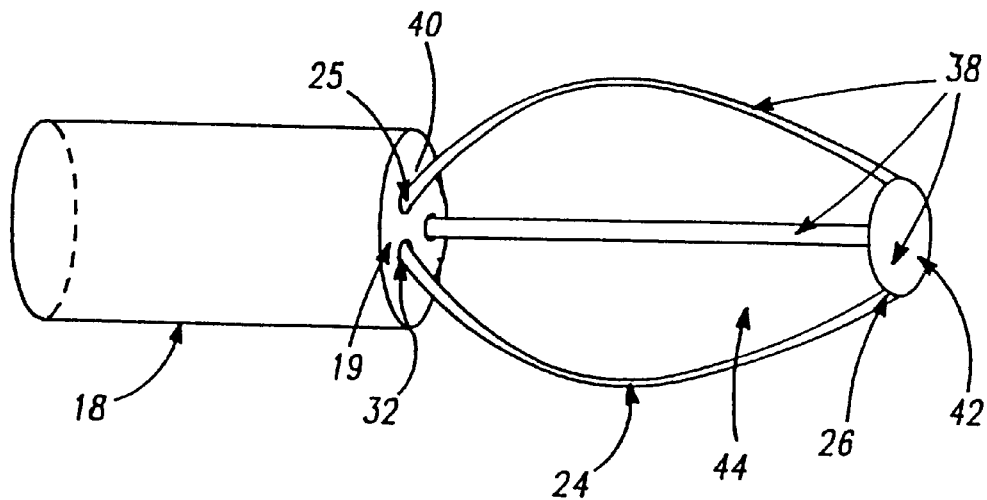
FIG. 4 illustrates a lateral view of the basket assembly used in an embodiment of the invention.

Referring now to FIG. 4, in another embodiment of the present invention, expansion device 20 comprises one or more elongated arms 24 that are joined at their proximal ends 25 and distal ends 26 to form a basket assembly 38. Proximal arm end 25 is attached to a supporting structure, which can be distal end 19 of introducer 18 or a proximal cap 40. Likewise, distal arm end 26 is also attached to a supporting structure which can be a distal basket cap 42 or introducer 18. Arms 24 are of a sufficient number, two or more, to sufficiently open and efface the folds of sphincter 16 to allow treatment with sphincter treatment apparatus 10, while preventing herniation of sphincter wall 30 into the spaces 44 between arms 24.

Arms 24 may form a variety of geometric shapes including, curved, rectangular, trapezoidal, triangular, or any combination thereof Also, arms 24 can have an outwardly bowed shaped memory for expanding basket assembly 38 into engagement with sphincter wall 30. Arms 24 may be preshaped at time of manufacture or shaped by the physician. Arms 24 can have a variety of cross sectional geometries including, circular, rectangular and crescent-shaped. The circumferential spacing of arms 24 can be symmetrical or asymmetrical with respect to a circumference around longitudinal axis 28. Suitable materials for arms 24 include spring steel, stainless steel, superelastic shape memory metals such as nitinol, or stiff shaft plastic tubing as is well known to those skilled in the art. Arms 24 may also be color-coded to facilitate their identification via visual medical imaging methods and equipment, such as endoscopic methods, which are well known to those skilled in the art.

Figure 5:
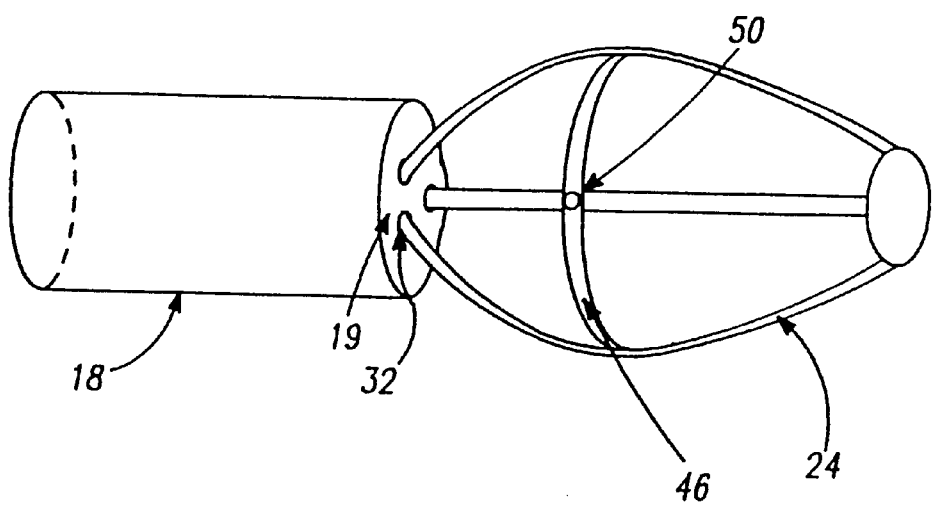
FIG. 5 is a lateral view of the basket assembly illustrating the placement of struts on the basket assembly.

In another embodiment of the invention depicted in FIG. 5, a supporting member 46 is attached to two or more arms 24. Supporting member 46, also called strut 46, can be attached to arms 24 along a circumference of basket assembly 38. Strut 46 may also contain apertures 50 in one or more places that extend through strut 46 to arm 24 as will be discussed herein. The cross sectional geometry of strut 46 can be rectangular, circular or crescent-shaped. Suitable materials for strut 46 include spring steel, stainless steel, superelastic shape memory metals such as nitinol, or stiff shaft plastic tubing as is well known to those skilled in the art.

Figure 6A:
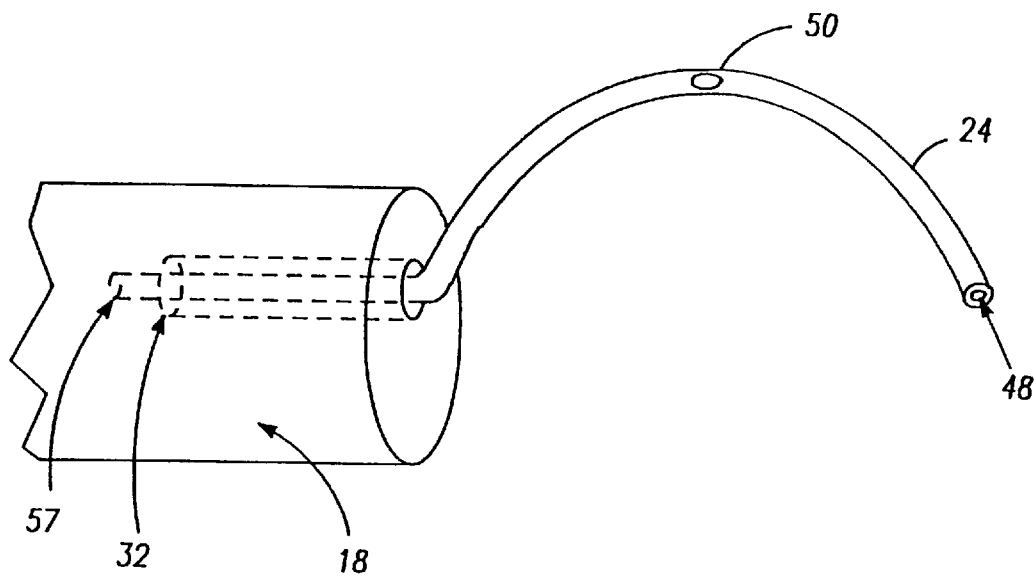
FIG. 6A is a lateral view of the junction between the basket arms and the introducer illustrating a lumen in the basket arm that can be used for the advancement of energy delivery devices.
Figure 6B:
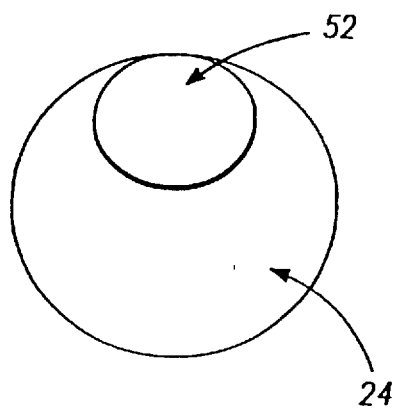
FIG. 6B is a frontal view of a basket arm in an alternative embodiment of the invention illustrating a track in the arm used to advance the movable wire.

Referring now to FIG. 6A, arms 24 may be solid or hollow with a continuous arm lumen 48 that may be coupled with introducer lumens 32. Also arms 24 may have one or more apertures 50 that may coupled to arm lumen 48. Coupled lumens 32 and 48, and apertures 50 provide a path for the delivery of a fluid or energy delivery device 22 from introducer 18 to the surface or interior of sphincter wall 30. As shown in FIG. 6B, arms 24 may also have a partially open channel 52, also called a track 52, that functions as a guide track for the travel of an advancement member (discussed herein) and/or energy delivery device 22 that permit the controlled placement of energy delivery devices 22 at or into sphincter wall 30. Referring now to FIG. 7, apertures 50 may have tapered sections 54 and/or stepped sections 56 in all or part of their length, that are used to control the penetration depth of energy delivery devices 22 into sphincter wall 30 as will be discussed herein. Energy delivery devices 22 may have similar tapered sections 54' and/or stepped sections 56'.

Figure 8A:
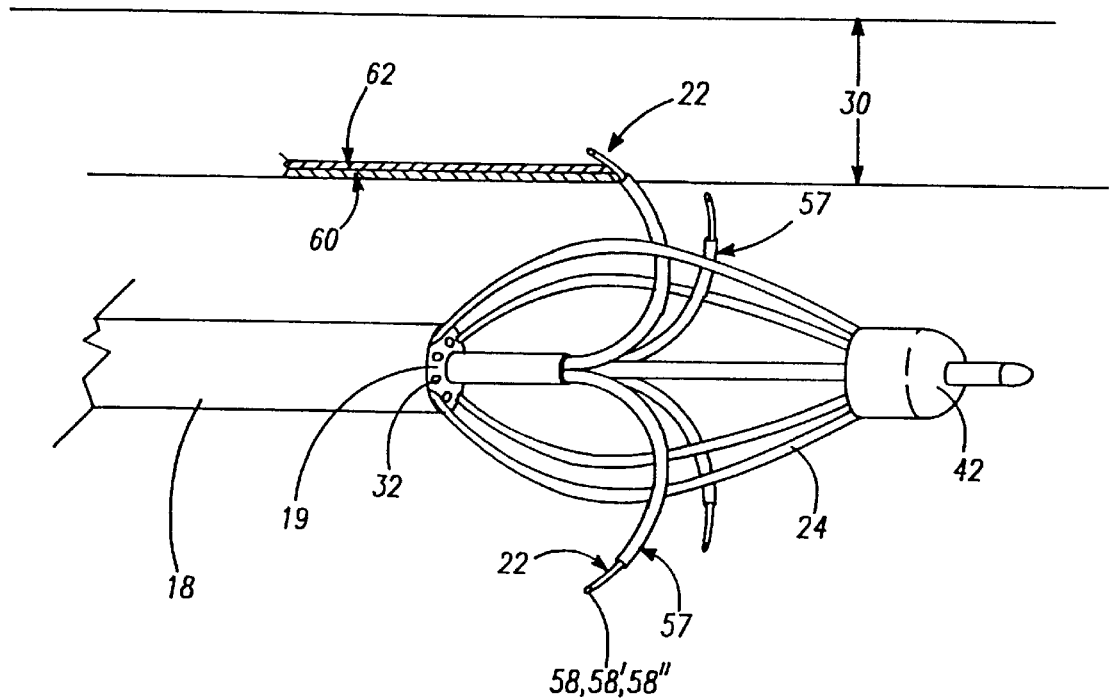
FIG. 8A is a lateral view of the basket assembly illustrating the use of the advancement member and introducer to position energy delivery devices into the sphincter wall.
Figure 8B:
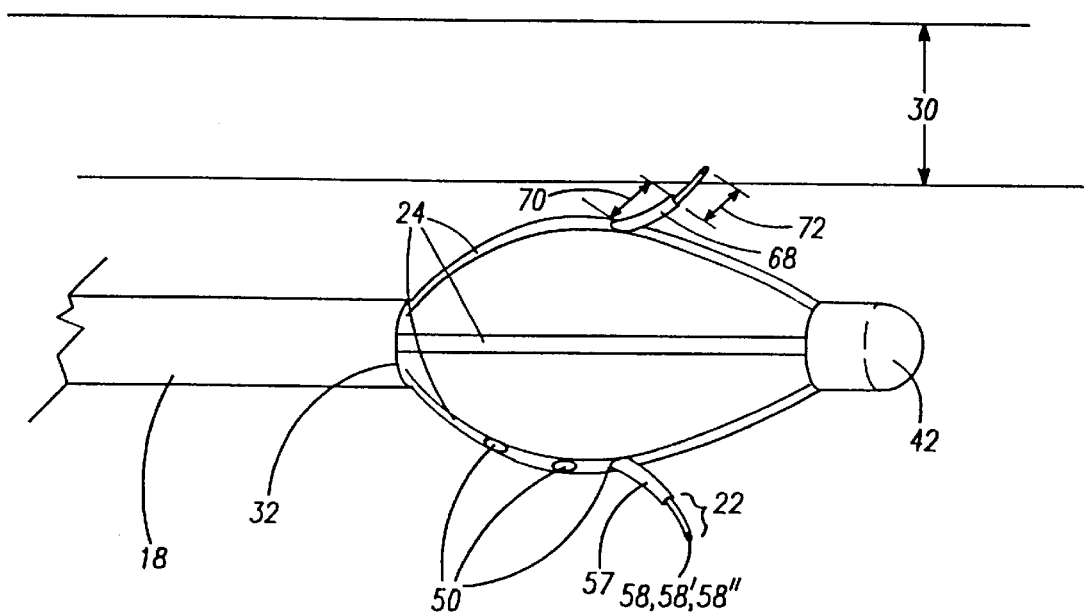
FIG. 8B is a lateral view of the basket assembly illustrating the use of the advancement member and basket arms to position energy delivery devices into the sphincter wall.

Referring now to FIGS. 8A and 8B, in another embodiment of the invention, energy delivery devices 22 can be coupled to an energy device delivery member 57, also called an advancement member 57. Advancement member 57 can be an insulated wire, an insulated guide wire, a plastic-coated stainless steel hypotube with internal wiring or a plastic catheter with internal wiring as is well known to those skilled in the art. Advancement member 57 is configured to be able to introduce energy delivery device 22 into sphincter wall 30 via introducer 18 (see FIG. 8A) or basket assembly 38 as will be discussed herein (see FIG. 8B). Advancement member 57 is of sufficient length to position energy delivery device 22 in the LES and/or stomach using a transoral approach. Typical lengths for advancement member 57 include a range of 40–180 cms.

Figure 9:
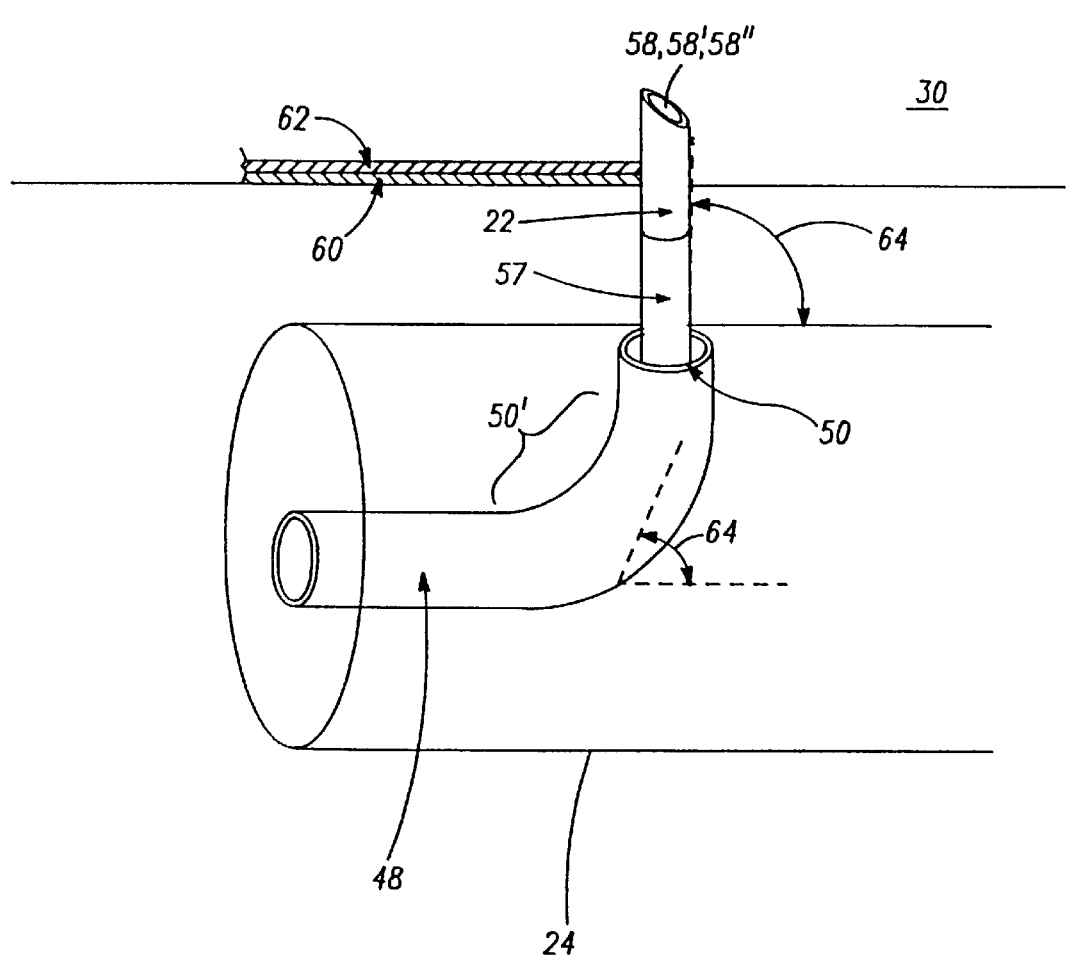
FIG. 9 is a cross sectional view illustrating the use of a needle electrode in combination with an angled aperture segment to select and maintain a constant penetration angle into the sphincter wall.

In another embodiment of the invention depicted in FIG. 9, energy delivery device 22 has a distal portion 58 that is configured to penetrate sphincter wall 30 with a minimum amount of tearing of the mucosal and submucosal layers 60 and 62 of sphincter 16. This is facilitated by maintaining a constant angle of penetration 64, also called penetration angle 64, of distal portion 58 into sphincter wall 30 during the time that energy delivery device 22 is advanced into sphincter wall 30. The typical range for penetration angle 64 lies between 1 and 90°. This can be accomplished through the use of a needle 58' for distal energy delivery device portion 58, coupled with an angled aperture segment 50' having a preselected penetration angle 64. Needle 58' is of sufficient sharpness and length to penetrate into the smooth muscle of sphincter wall 30. In a further embodiment, needle 58' can be a needle electrode 58". Distal portion 58, including needle 58' and needle electrode 58 can also be stepped or tapered to enable control of energy delivery device (see FIG. 7). Suitable materials for needle 58' and needle electrodes 58" include 304 stainless steel and other metals known to those skilled in the art.

Figure 10A:
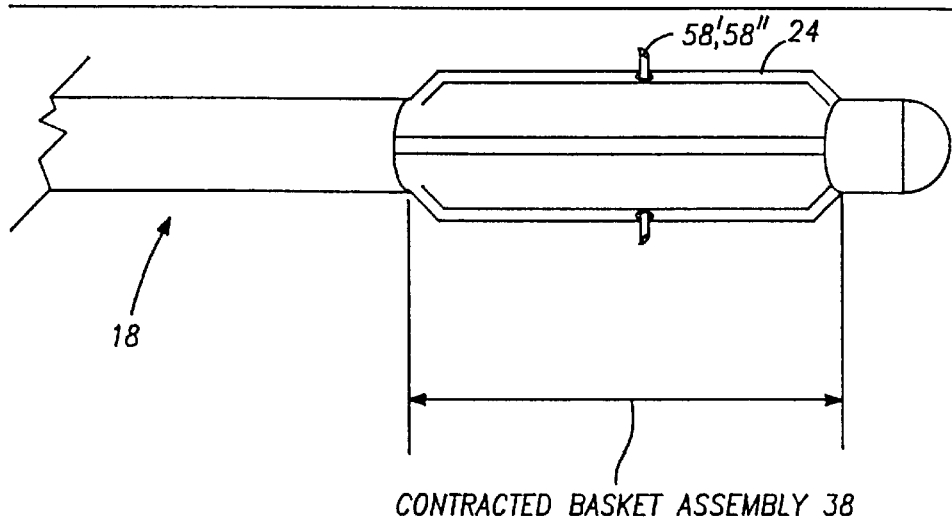
FIGS. 10a and 10b are lateral views illustrating the placement of needle electrodes into the sphincter wall by expansion of the basket assembly.
Figure 10B:
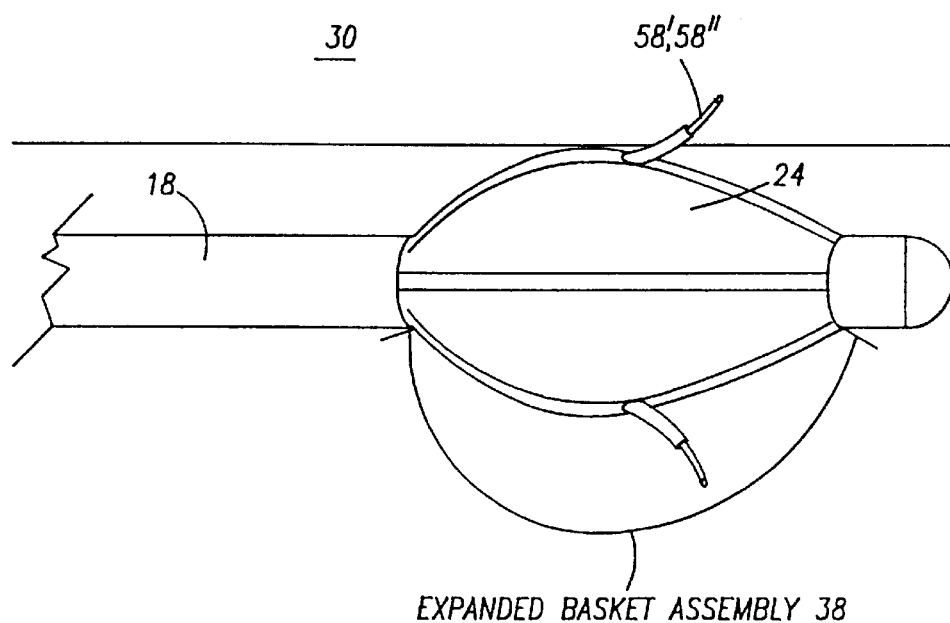

In another embodiment of the invention, energy delivery device 22 is coupled to arm 24. As shown in FIG. 10, this can be accomplished by attaching needle 58' to arm 24. When sphincter treatment apparatus 10 is properly positioned at the treatment site 12, needles 58' are deployed by expansion of basket assembly 38, resulting in the protrusion of needle 58' into the smooth muscle tissue of sphincter wall 30 (see FIG. 10). Referring back to FIG. 9, coupling can also be accomplished by employing arm 24 to introduce energy delivery device 22 into sphincter wall 30 via use of arm lumen 48.

Turning now to a discussion of energy delivery, suitable power sources and energy delivery devices 22 that can be employed in one or more embodiments of the invention include or more of the following: (i) a radio-frequency (RF) source coupled to an RF electrode, (ii) a coherent source of light coupled to an optical fiber, (iii) an incoherent light source coupled to an optical fiber, (iv) a heated fluid coupled to a catheter with a closed channel configured to receive the heated fluid, (v) a heated fluid coupled to a catheter with an open channel configured to receive the heated fluid, (vi) a cooled fluid coupled to a catheter with a closed channel configured to receive the cooled fluid, (vii) a cooled fluid coupled to a catheter with an open channel configured to receive the cooled fluid, (viii) a cryogenic fluid, (ix) a resistive heating source, (x) a microwave source providing energy from 915 MHz to 2.45 GHz and coupled to a microwave antenna, or (xi) an ultrasound power source coupled to an ultrasound emitter, wherein the ultrasound power source produces energy in the range of 300 KHZ to 3 GHz. For ease of discussion for the remainder of this application, the power source utilized is an RF source and energy delivery device 22 is one or more RF electrodes 66, also described as electrodes 66. However, all of the other herein mentioned power sources and energy delivery devices are equally applicable to sphincter treatment apparatus 10.

For the case of RF energy, RF electrode 66 may be operated in either bipolar or monopolar mode with a ground pad electrode. In a monopolar mode of delivering RF energy, a single electrode 66 is used in combination with an indifferent electrode patch that is applied to the body to form the other electrical contact and complete an electrical circuit. Bipolar operation is possible when two or more electrodes 66 are used. Multiple electrodes 66 may be used. These electrodes may be cooled as described herein. Electrodes 66 can be attached to advancement member 57 by the use of soldering methods which are well known to those skilled in the art.

Referring now to FIG. 11, RF electrodes 66 can have an insulating layer 68, covering an insulated segment 70 except for an exposed segment 72. For purposes of this disclosure, an insulator or insulation layer is a barrier to either thermal or electromagnetic energy flow including RF energy flow. Insulated segment 70 is of sufficient length to extend into sphincter wall 30 and minimize the transmission of RF energy to a protected site 74 near or adjacent to insulated segment 70. Typical lengths for insulated segment 70 include, but are not limited to, 1–4 mm. Suitable materials for insulating layer 68 include electrically insulating plastics and other materials well known to those skilled in the art.

In another embodiment of the invention, the depth of penetration of energy delivery device 22 into sphincter wall 30 is controllable. This can be accomplished by the selection and control of the dimensional relationships (e.g. the amount of clearance between inner and outer diameters) of energy delivery devices 22 and/or advancement member 57 to one or more of the following elements: arm lumen 48, apertures 50 and track 52. Control of penetration depth can also be accomplished through the use of tapered and/or stepped sections in one or more of the preceding elements as is discussed herein. In another embodiment, penetration depth control can be accomplished by the use of one or more of a variety of positional control means, known to those skilled in the art, that are coupled to sphincter treatment apparatus 10. Such positional control means include stepper motor systems, indexing mechanisms and micromanipulators.

Figure 12:
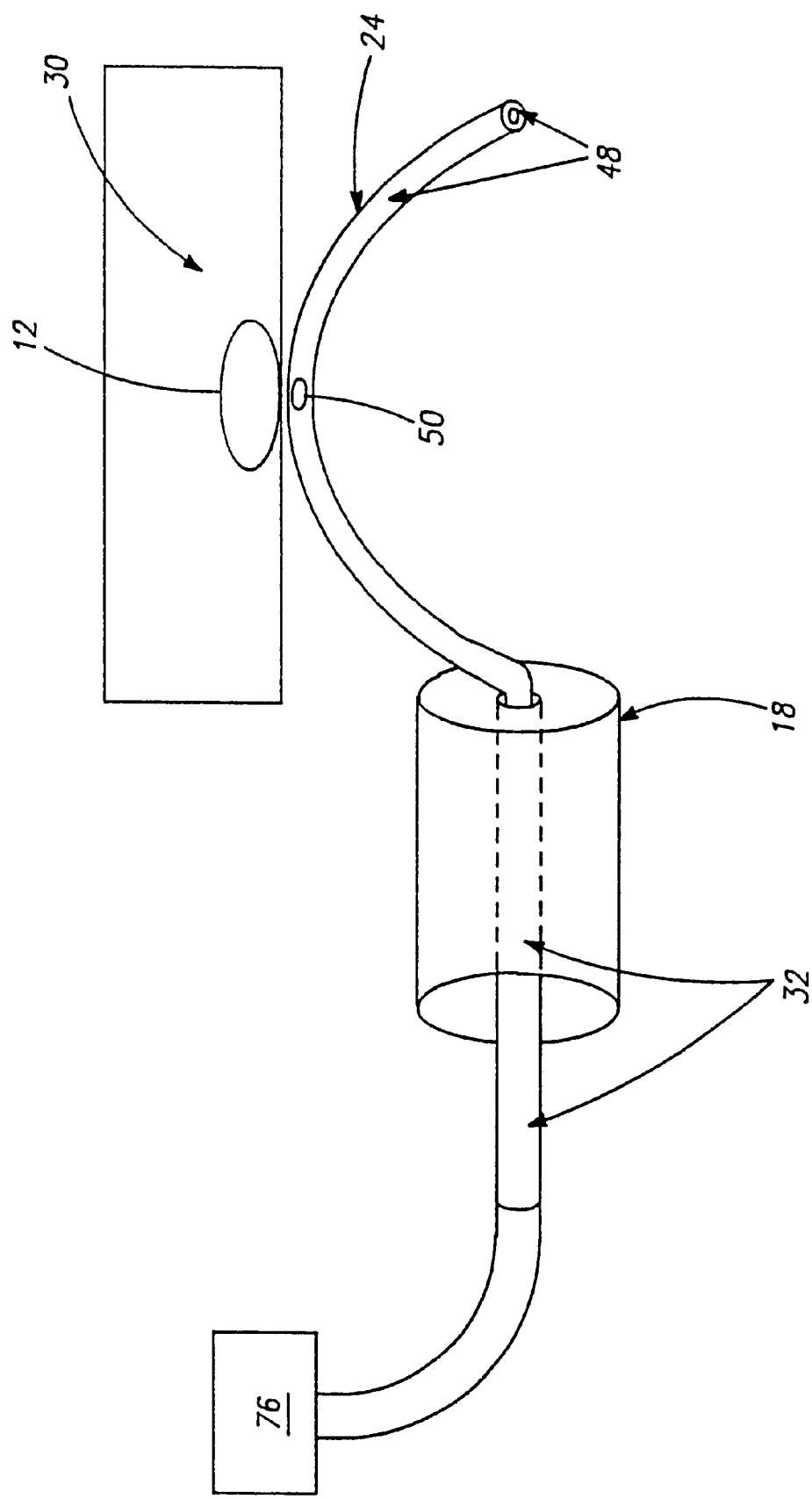
FIG. 12 depicts the fluid source and flow path to deliver fluid to treatment site using the introducer.

Referring now to FIG. 12, in another embodiment of the invention, fluid can be delivered to treatment site 12 via introducer 18. This is accomplished by the coupling of introducer 18 to a fluid source 76 via introducer lumen 32.

Figure 13:
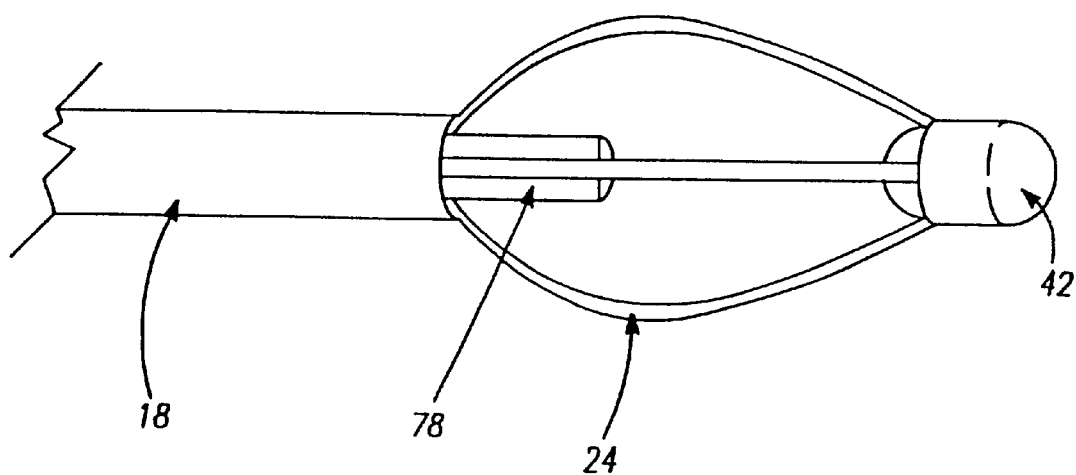
FIG. 13 is a cross sectional view illustrating a visualization device coupled to an embodiment of the invention.

Referring now to FIG. 13, another embodiment of sphincter treatment apparatus 10 includes a visualization device 78 coupled to introducer 18. Visualization device 78 can include a combination of one or more of the following: a viewing scope, an expanded eyepiece, fiber optics (both imaging and illuminating fibers), video imaging devices and the like.

Figure 14:
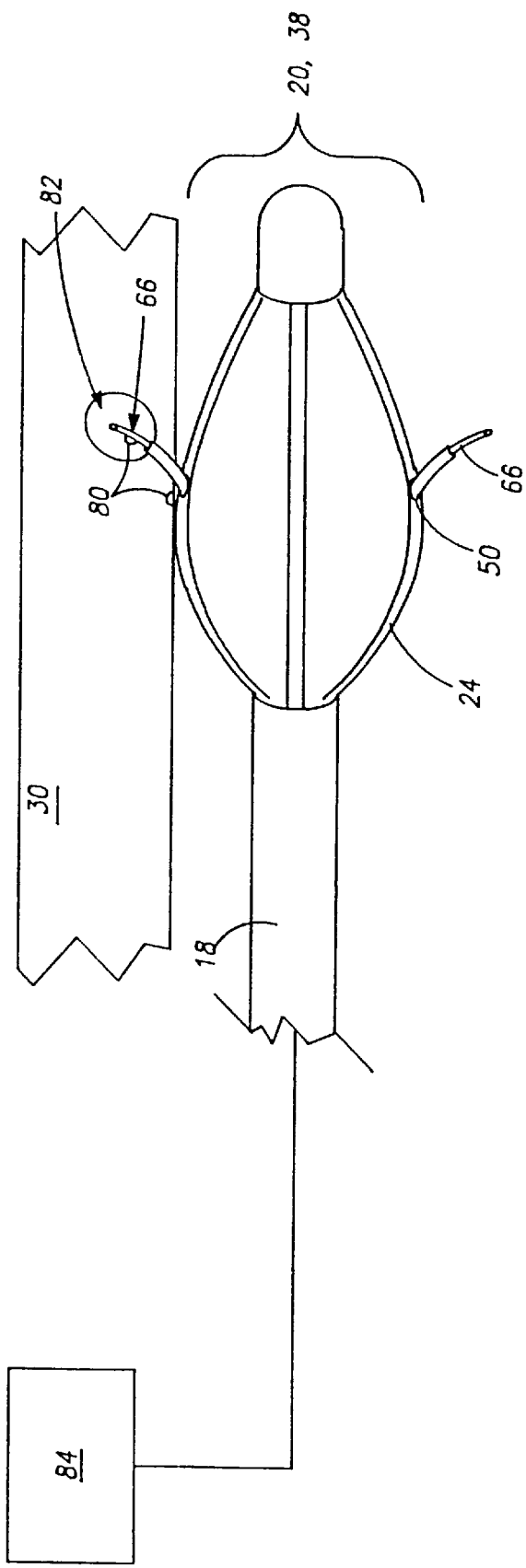
FIG. 14 is an enlarged lateral view illustrating the placement of sensors on/adjacent the energy delivery device and the coupling of sensors to a feedback control system.

As shown in FIG. 14, one or more sensors 80 may be positioned adjacent to or on electrode 66 for sensing the physical properties of sphincter tissue at treatment site 12. Sensors 80 permit accurate determination of the physical properties of sphincter wall 30 at an electrode-tissue interface 82. Such physical properties include temperature, electrical conductivity, electrical capacitance, thermal conductivity, density, thickness, strength, elasticity, moisture content, optical reflectance, optical transmittance, optical absorption acoustical impedance and acoustical absorption. Sensors 80 can be positioned at any position on expansion device 20, electrode 66 or basket assembly 38. Suitable sensors that may be used for sensor 80 include: thermocouples, fiber optics, photomultipliers, resistive wires, thermocouple IR detectors, thin film sensors, anemometric sensors and ultrasound sensors. Sensor 80 can be coupled to a feedback control system 84, described herein. The coupling of sensor 80 to feedback control system 84 can be used to regulate the delivery of energy, fluids and gases to one or more of the following locations: treatment site 12, sphincter wall 30, and electrode tissue interface 82.

Figure 15:
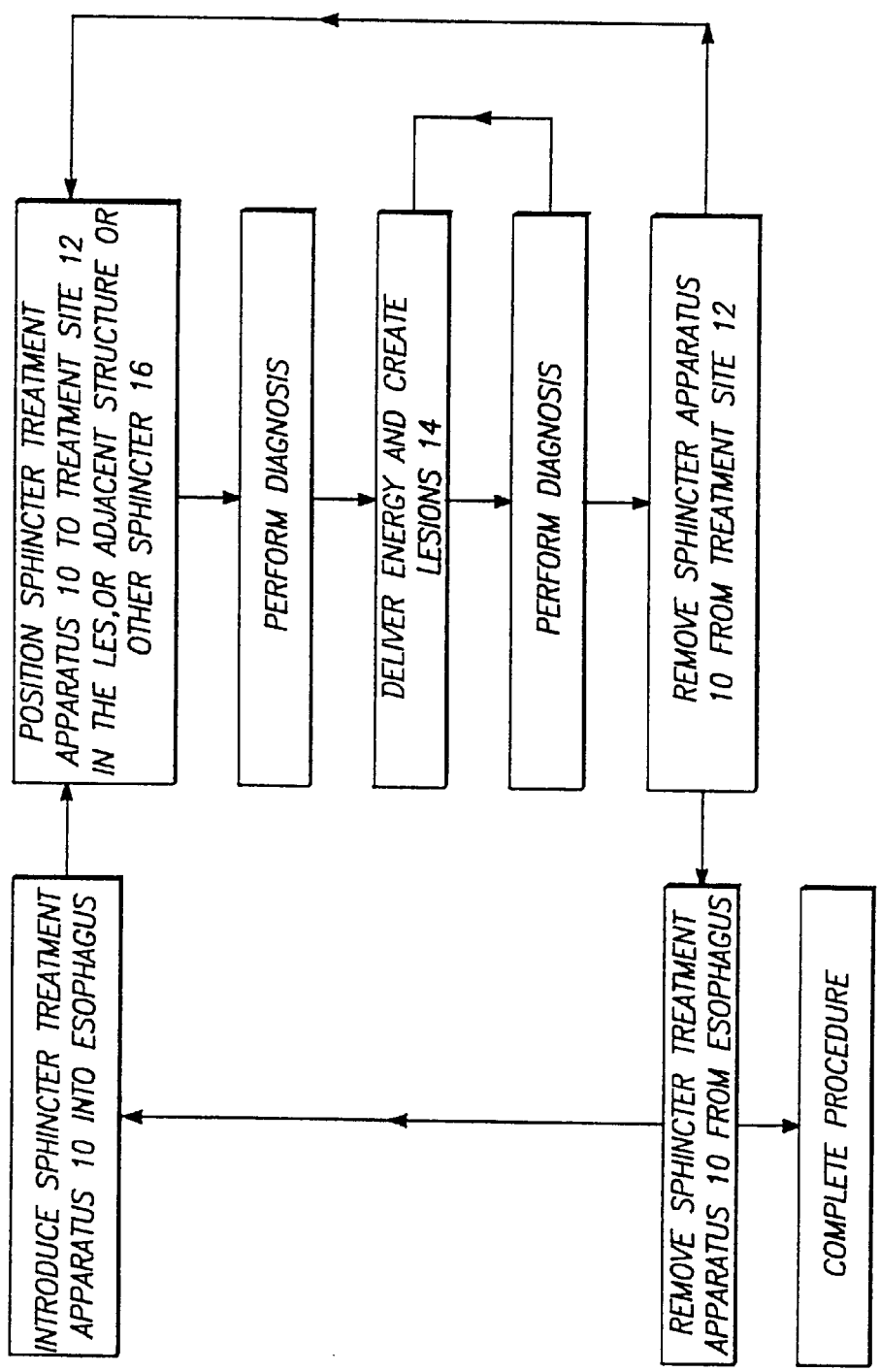
FIG. 15 is a flow chart illustrating a sphincter treatment method using the apparatus of the present invention.

FIG. 15 is a flow chart illustrating a method for using sphincter treatment apparatus 10. First, sphincter treatment apparatus 10 is introduced into the esophagus under local anesthesia and positioned at treatment site 12. Sphincter treatment apparatus 10 can be introduced into the esophagus by itself or through a lumen in an endoscope (not shown), such as disclosed in U.S. Pat. Nos. 5,448,990 and 5,275,608, incorporated herein by reference, or a similar esophageal access device known to those skilled in the art. Basket assembly 38 is expanded as described herein. This serves to temporarily dilate the LES sufficiently to efface all or a portion of the folds of the LES. In an alternative embodiment, esophageal dilation and subsequent LES fold effacement can be accomplished by insufflation of the esophagus (a known technique) using gas introduced into the esophagus through introducer lumen 32, an endoscope, or others esophageal access devices known to those skilled in the art. Once treatment is completed, basket assembly 38 is returned to its predeployed or contracted state and sphincter treatment apparatus 10 is withdrawn from the esophagus. This results in the LES returning to approximately its pretreatment state and diameter. It will be appreciated that the above procedure is applicable in whole or part to the treatment of other sphincters in the body.

Figure 16:
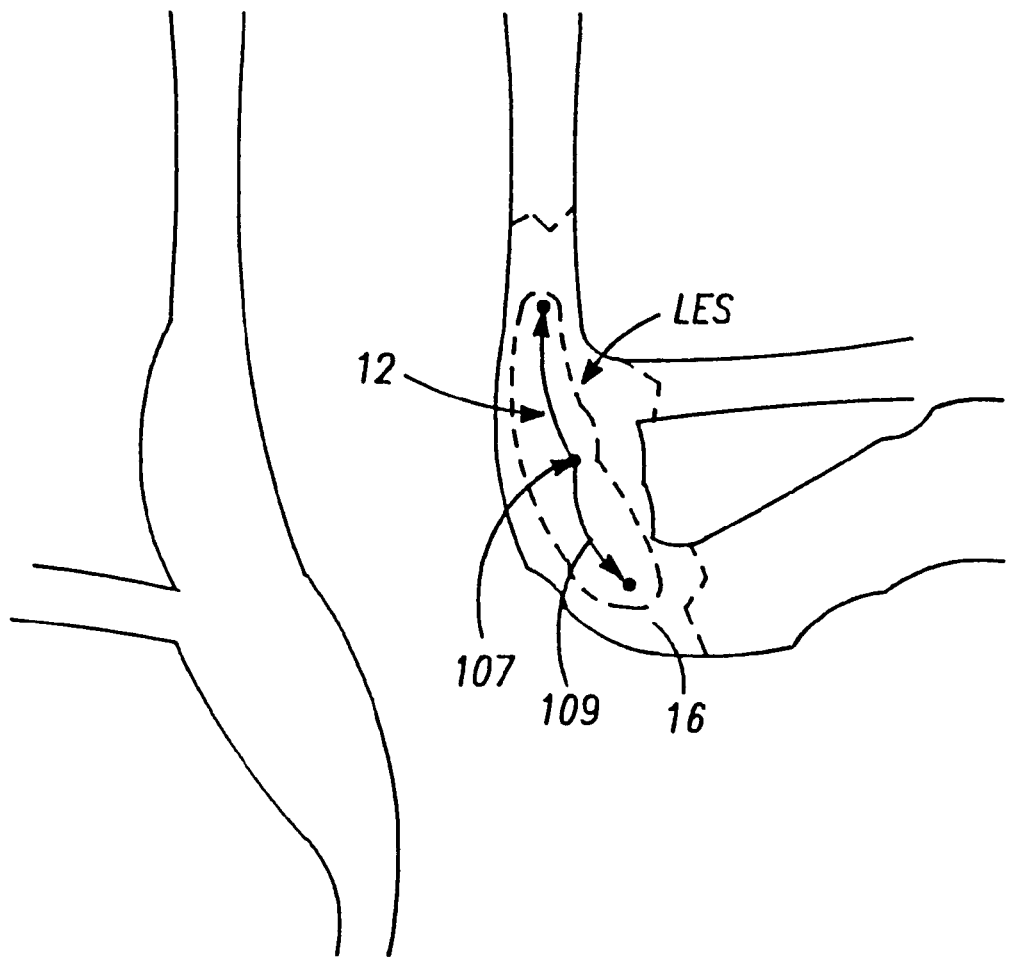
FIG. 16 is a lateral view of sphincter smooth muscle tissue illustrating electrical foci and electrically conductive pathways for the origination and conduction of aberrant electrical signals in the smooth muscle of the lower esophageal sphincter or other tissue.

The diagnostic phase of the procedure then begins and can be performed using a variety of diagnostic methods known to those skilled in the art including the following: (i) visualization of the interior surface of the esophagus via an endoscope or other viewing apparatus inserted into the esophagus, (ii) visualization of the interior morphology of the esophageal wall using ultrasonography to establish a baseline for the tissue to be treated, (iii) impedance measurement to determine the electrical conductivity between esophageal mucosal and submucosal layers 60 and 62 and sphincter treatment apparatus 10, and (iv) measurement and surface mapping of electropotential signals of the LES and surrounding anatomical structures during varying time intervals which may include such events as depolarization, contraction and repolarization of gastroesophageal smooth muscle tissue. This latter technique is done to determine target treatment sites 12 in the LES or adjoining anatomical structures that are acting as electrical foci 107 or electrically conductive pathways 109 for abnormal or inappropriate polarization and relaxation of the smooth muscle of the LES (Refer to FIG. 16).

After diagnosis, the treatment phase of the procedure begins. In this phase of the procedure, the delivery of energy to treatment site 12 can be conducted under feedback control, manually or by a combination of both. Feedback control (described herein) enables sphincter treatment apparatus 10 to be positioned and retained in the esophagus during treatment with minimal attention by the physician. Electrodes 66 can be multiplexed in order to treat the entire targeted treatment site 12 or only a portion thereof. Feedback can be included and is achieved by the use of one or more of the following methods: (i) visualization, (ii) impedance measurement, (iii) ultrasonography, (iv) temperature measurement; and, (v) contractile force measurement via manometry. The feedback mechanism permits the selected on-off switching of different electrodes 66 in a desired pattern, which can be sequential from one electrode 66 to an adjacent electrode 66, or can jump around between non-adjacent electrodes 66. Individual electrodes 66 are multiplexed and volumetrically controlled by a controller.

Figure 17:
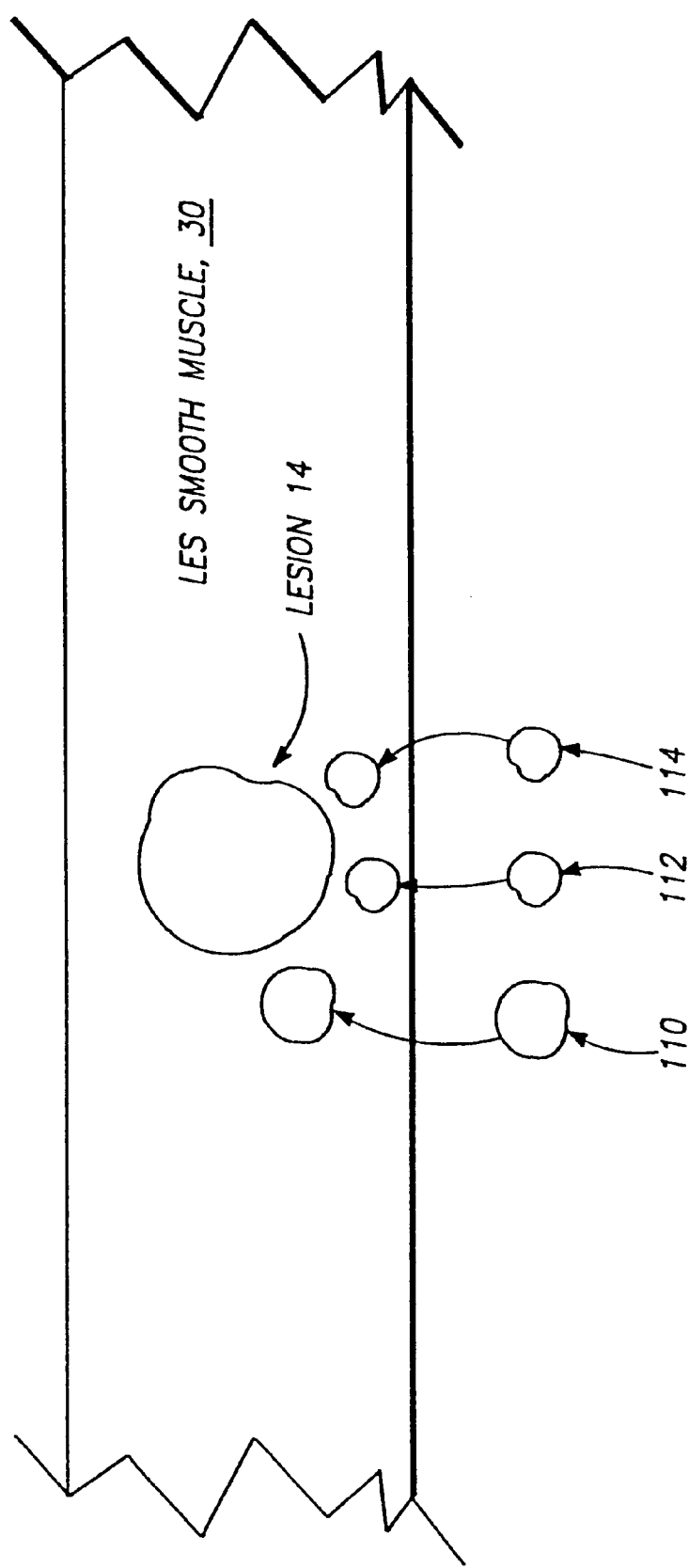
FIG. 17 is a lateral view of a sphincter wall illustrating the infiltration of tissue healing cells into a lesion in the smooth tissue of a sphincter following treatment with the sphincter treatment apparatus of the present invention.
Figure 18:
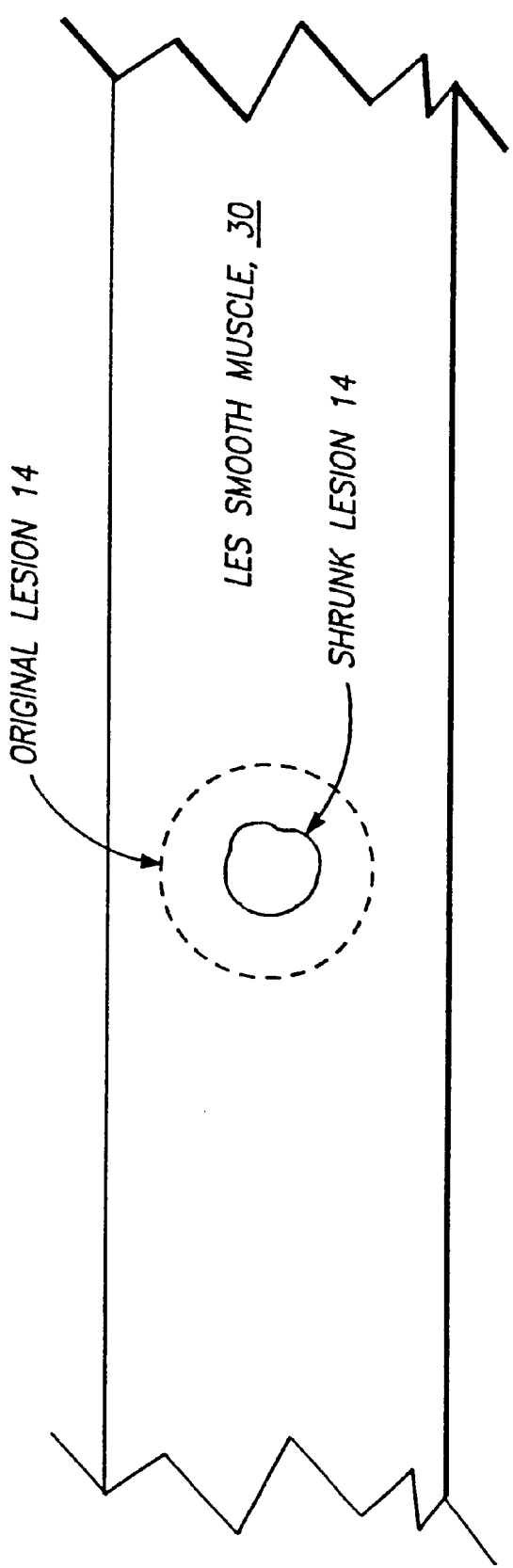
FIG. 18 is a view similar to that of FIG. 17 illustrating shrinkage of the lesion site caused by cell infiltration.
Figure 19:
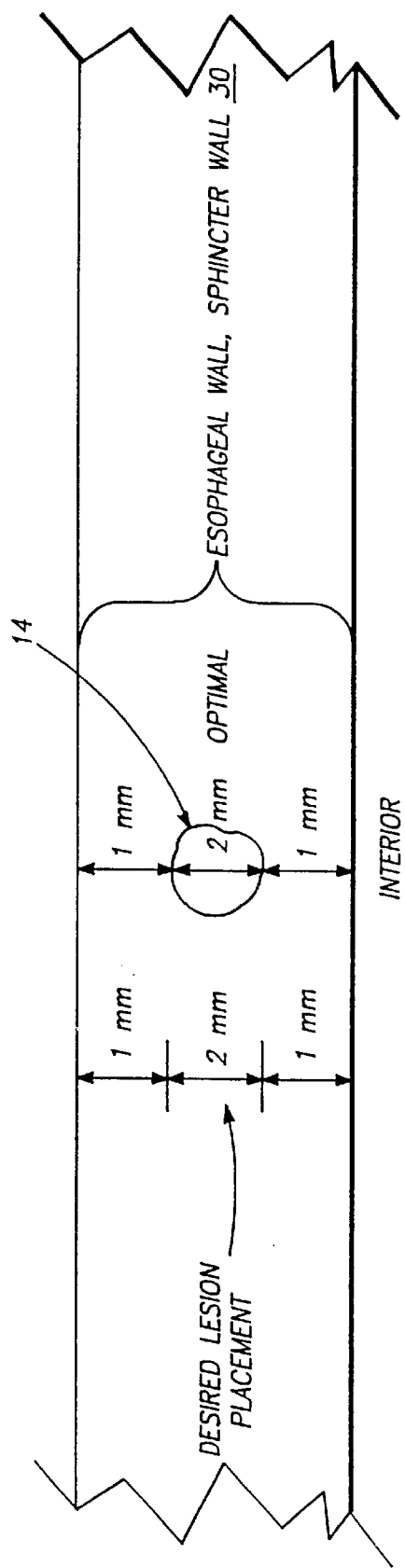
FIG. 19 is a lateral view of the esophageal wall illustrating the preferred placement of lesions in the smooth muscle layer of a esophageal sphincter.
Figure 20B:
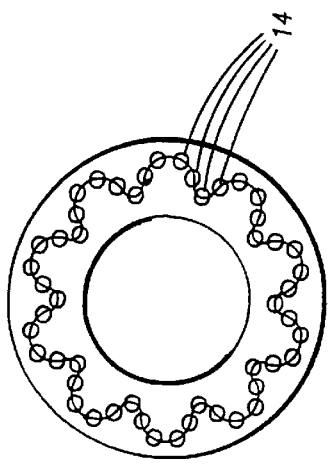
FIGS. 20A–D are lateral views of the sphincter wall illustrating various patterns of lesions created by the apparatus of the present invention.
Figure 20D:
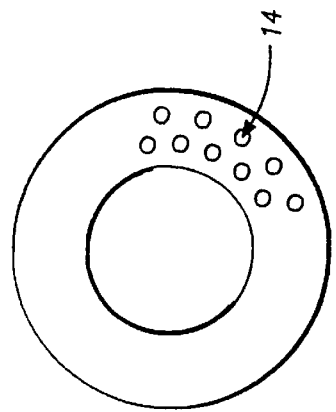
Figure 20A:
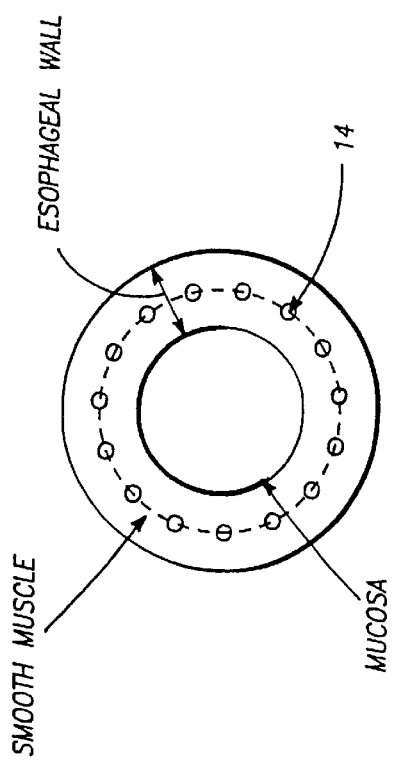
Figure 20C:
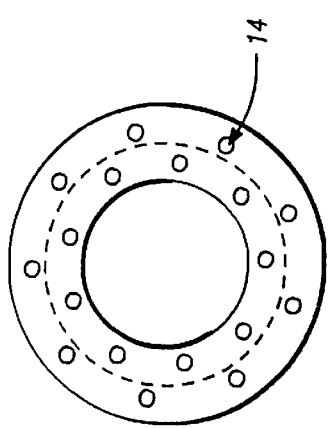

The area and magnitude of cell injury in the LES or sphincter 16 can vary. However, it is desirable to deliver sufficient energy to the targeted treatment site 12 to be able to achieve tissue temperatures in the range of 55–95° C. and produce lesions 14 at depths ranging from 1–4 mms from the interior surface of the LES or sphincter wall 30. Typical energies delivered to the esophageal or stomach wall include, but are not limited to, a range between 100 and 50,000 joules per electrode 66. It is also desirable to deliver sufficient energy such that resulting lesions 14 have a sufficient magnitude and area of cell injury to cause an infiltration of lesion 14 by fibroblasts 110, myofibroblasts 112, macrophages 114 and other cells involved in the tissue healing process (refer to FIG. 17). As shown in FIG. 18, these cells cause a contraction of tissue around lesion 14, decreasing its volume and/or altering the biomechanical properties at lesion 14 so as to result in a tightening of the LES or sphincter 16. These changes are reflected in transformed lesion 14'. The diameter of lesions 14 can vary between 0.1 to 4 mm. It is preferable that lesions 14 are less than 4 mms in less than 4 mms in diameter in order to reduce the risk of thermal damage to mucosal and submucosal layers 60 and 62. In one embodiment, a 2 mm diameter lesion 14 centered in the wall of the smooth muscle provides a 1 mm buffer zone on either side of lesion 14 to prevent damage to mucosal and submucosal layers 60 and 62 and the adventitia (not shown), while still allowing for cell infiltration and subsequent sphincter tightening on approximately 50% of the thickness of the wall of the smooth muscle (refer to FIG. 19).

It is desirable that lesions 14 are predominantly located in the smooth muscle layer of selected sphincter 16 at the depths ranging from 1 to 4 mm from the interior surface of sphincter wall 30. However, lesions 14 can vary both in number and position within sphincter wall 30. It may be desirable to produce a pattern of multiple lesions 14 within the sphincter smooth muscle tissue in order to obtain a selected degree of tightening of the LES or other sphincter 16. Typical lesion patterns shown in FIGS. 20 A–D include, but are not limited to, (i) a concentric circle of lesions 14 all at fixed depth in the smooth muscle layer evenly spaced along the radial axis of sphincter 16, (ii) a wavy or folded circle of lesions 14 at varying depths in the smooth muscle layer evenly spaced along the radial axis of sphincter 16, (iii) lesions 14 randomly distributed at varying depths in the smooth muscle, but evenly spaced in a radial direction and, (iv) an eccentric pattern of lesions 14 in one or more radial locations in the smooth muscle wall. Accordingly, the depth of RF and thermal energy penetration into sphincter 16 is controlled and selectable. The selective application of energy to sphincter 16 may be the even delivery of RF energy to the entire targeted treatment site 12, a portion of it, or applying different amounts of RF energy to different sites depending on the condition of sphincter 16. If desired, the area of cell injury can be substantially the same for every treatment event.

A second diagnostic phase may be included after the treatment is completed. This provides an indication of LES tightening treatment success, and whether or not a second phase of treatment, to all or only a portion of the esophagus, now or at some later time, should be conducted. The second diagnostic phase is accomplished through one or more of the following methods: (i) visualization, (ii) measuring impedance, (iii) ultrasonography, (iv) temperature measurement, or (v) measurement of LES tension and contractile force via manometry.

Figure 21:
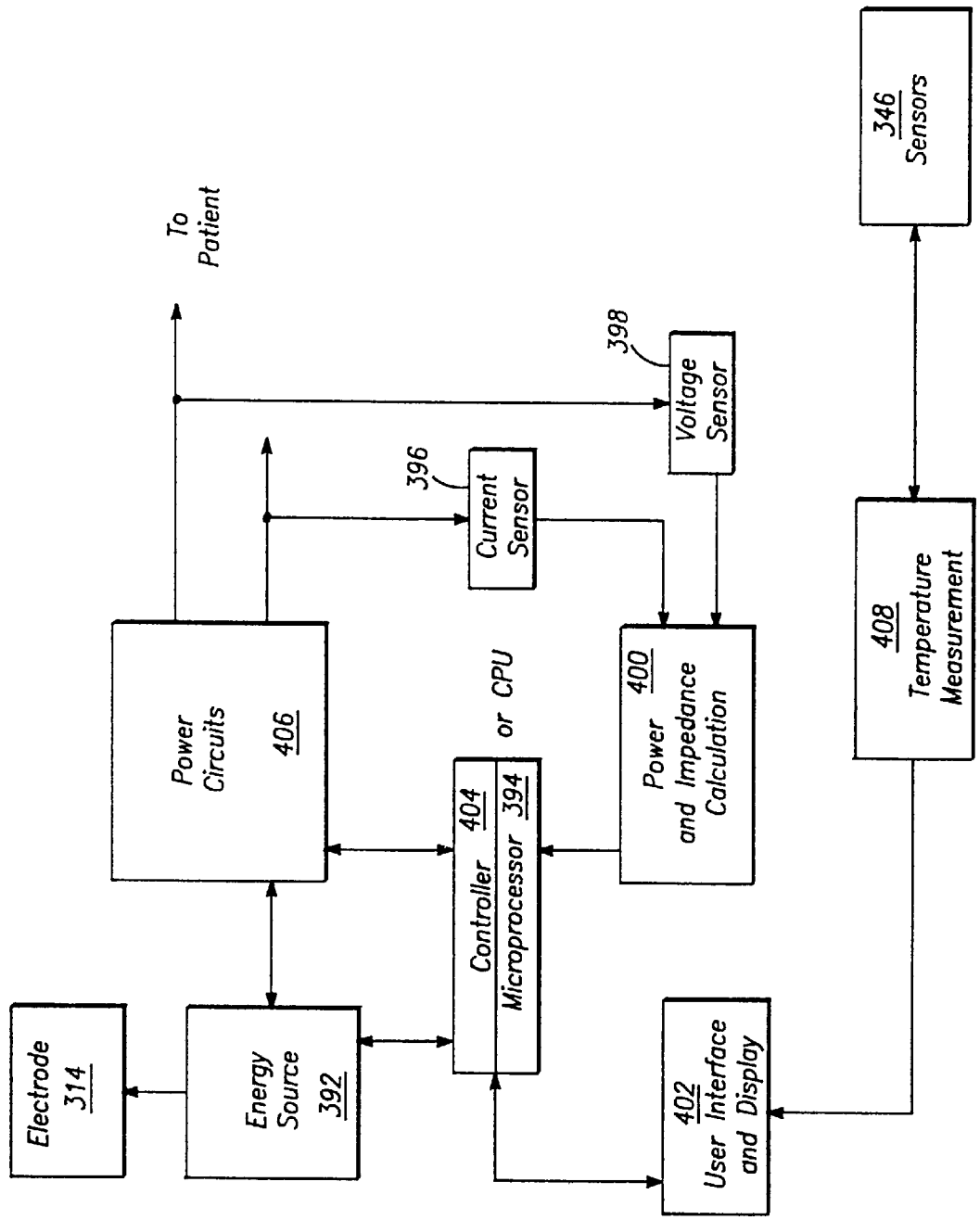
FIG. 21 depicts a block diagram of the feed back control system that can be used with an embodiment of the invention.

In one embodiment of the invention, sensor 80 is coupled to an open or closed loop feedback control system 84. Referring now to FIG. 21, an open or closed loop feedback system 84 couples sensor 80, now described as sensor 346, to an energy source 392. In this embodiment, an energy delivery device 314 is one or more RF electrodes 314; however, in various other embodiments, energy delivery device 314 may include others described herein. Similarly, in this embodiment, sensor 346 senses temperature, but in various other embodiments, sensor 346 may sense other physical properties described herein.

The temperature of the tissue, or of RF electrode 314, is monitored, and the output power of energy source 392 adjusted accordingly. The physician can, if desired, override the closed or open loop system 84. A microprocessor 394 can be included and incorporated in the closed or open loop system to switch power on and off, as well as modulate the power. The closed loop system 84 utilizes microprocessor 394 to serve as a controller, monitor the temperature, adjust the RF power, analyze the result, refeed the result, and then modulate the power.

With the use of sensor 346 and feedback control system 84, tissue adjacent to RF electrode 314 can be maintained at a desired temperature for a selected period of time without causing a shut down of the power circuit to electrode 314 due to the development of excessive electrical impedance at electrode 314 or adjacent tissue. Each RF electrode 314 is connected to resources which generate an independent output. The output maintains a selected energy at RF electrode 314 for a selected length of time.

Current delivered through RF electrode 314 is measured by current sensor 396. Voltage is measured by voltage sensor 398. Impedance and power are then calculated at power and impedance calculation device 400. These values can then be displayed at user interface and display 402. Signals representative of power and impedance values are received by a controller 404.

A control signal is generated by controller 404 that is proportional to the difference between an actual measured value, and a desired value. The control signal is used by power circuits 406 to adjust the power output an appropriate amount in order to maintain the desired power delivered at respective RF electrodes 314.

In a similar manner, temperatures detected at sensor 346 provide feedback for maintaining a selected power. Temperature at sensor 346 is used as a safety means to interrupt the delivery of power when maximum pre-set temperatures are exceeded. The actual temperatures are measured at temperature measurement device 408, and the temperatures are displayed at user interface and display 402. A control signal is generated by controller 404 that is proportional to the difference between an actual measured temperature and a desired temperature. The control signal is used by power circuits 406 to adjust the power output an appropriate amount in order to maintain the desired temperature delivered at the sensor 346. A multiplexer can be included to measure current, voltage and temperature, at the sensor 346, and energy can be delivered to RF electrode 314 in monopolar or bipolar fashion.

Controller 404 can be a digital or analog controller, or a computer with software. When controller 404 is a computer it can include a CPU coupled through a system bus. This system can include a keyboard, a disk drive, or other non-volatile memory systems, a display, and other peripherals, as are known in the art. Also coupled to the bus is a program memory and a data memory.

User interface and display 402 includes operator controls and a display. Controller 404 can be coupled to imaging systems including, but not limited to, ultrasound, CT scanners, X-ray, MRI, mammographic X-ray and the like. Further, direct visualization and tactile imaging can be utilized.

The output of current sensor 396 and voltage sensor 398 are used by controller 404 to maintain a selected power level at RF electrode 314. The amount of RF energy delivered controls the amount of power. A profile of the power delivered to electrode 314 can be incorporated in controller 404 and a preset amount of energy to be delivered may also be profiled.

Circuitry, software and feedback to controller 404 result in process control, the maintenance of the selected power setting which is independent of changes in voltage or current, and is used to change the following process variables: (i) the selected power setting, (ii) the duty cycle (e.g., on-off time), (iii) bipolar or monopolar energy delivery; and, (iv) fluid delivery, including flow rate and pressure. These process variables are controlled and varied, while maintaining the desired delivery of power independent of changes in voltage or current, based on temperatures monitored at sensor 346.

Figure 22:
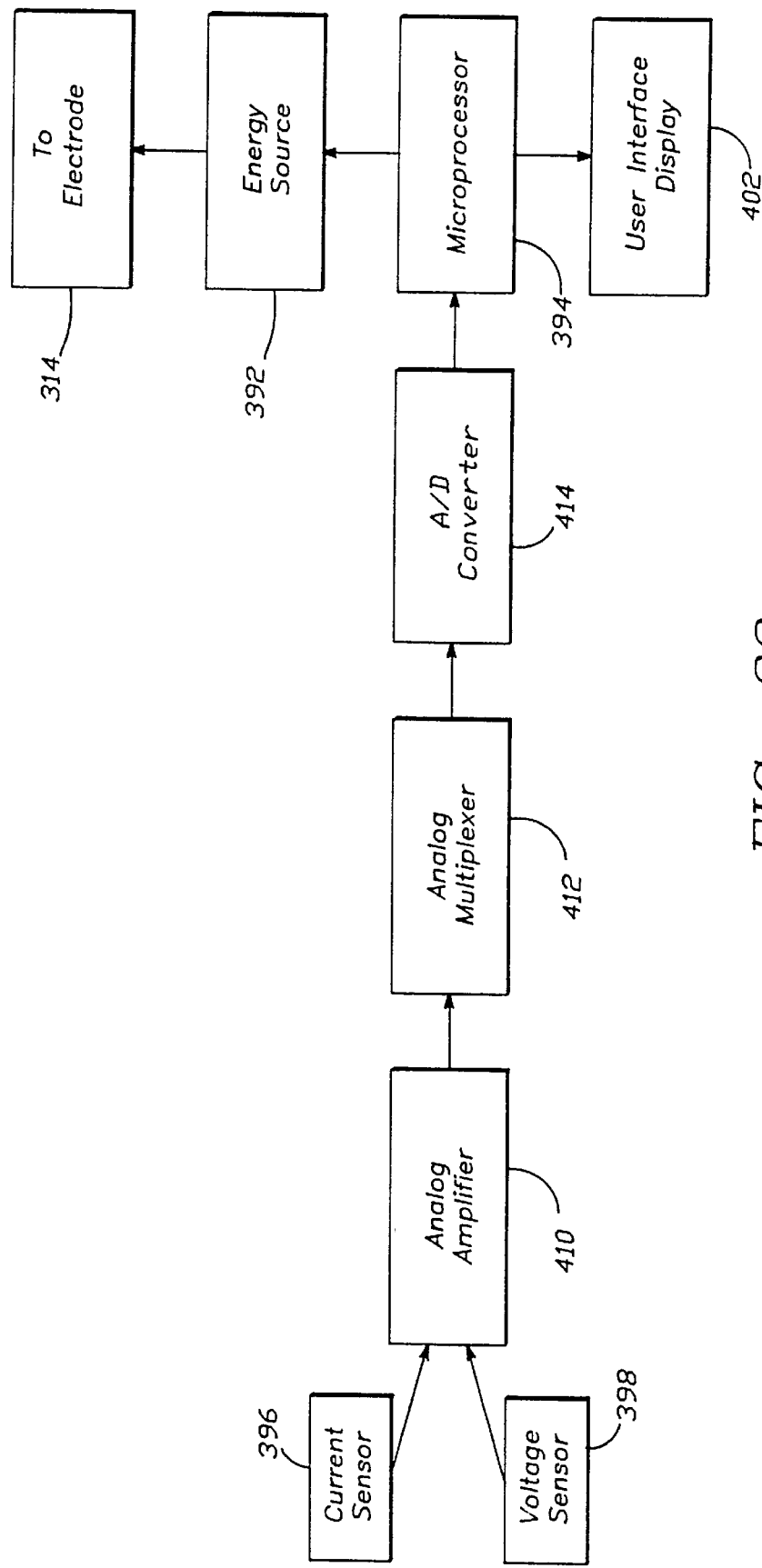
FIG. 22 depicts a block diagram of an analog amplifier, analog multiplexer and microprocessor used with the feedback control system of FIG. 21.

Referring now to FIG. 22, current sensor 396 and voltage sensor 398 are connected to the input of an analog amplifier 410. Analog amplifier 410 can be a conventional differential amplifier circuit for use with sensor 346. The output of analog amplifier 410 is sequentially connected by an analog multiplexer 412 to the input of A/D converter 414. The output of analog amplifier 410 is a voltage which represents the respective sensed temperatures. Digitized amplifier output voltages are supplied by A/D converter 414 to microprocessor 394. Microprocessor 394 may be a type 68HCII available from Motorola. However, it will be appreciated that any suitable microprocessor or general purpose digital or analog computer can be used to calculate impedance or temperature.

Microprocessor 394 sequentially receives and stores digital representations of impedance and temperature. Each digital value received by microprocessor 394 corresponds to different temperatures and impedances.

Calculated power and impedance values can be indicated on user interface and display 402. Alternatively, or in addition to the numerical indication of power or impedance, calculated impedance and power values can be compared by microprocessor 394 to power and impedance limits. When the values exceed predetermined power or impedance values, a warning can be given on user interface and display 402, and additionally, the delivery of RF energy can be reduced, modified or interrupted. A control signal from microprocessor 394 can modify the power level supplied by energy source 392.

Figure 23:
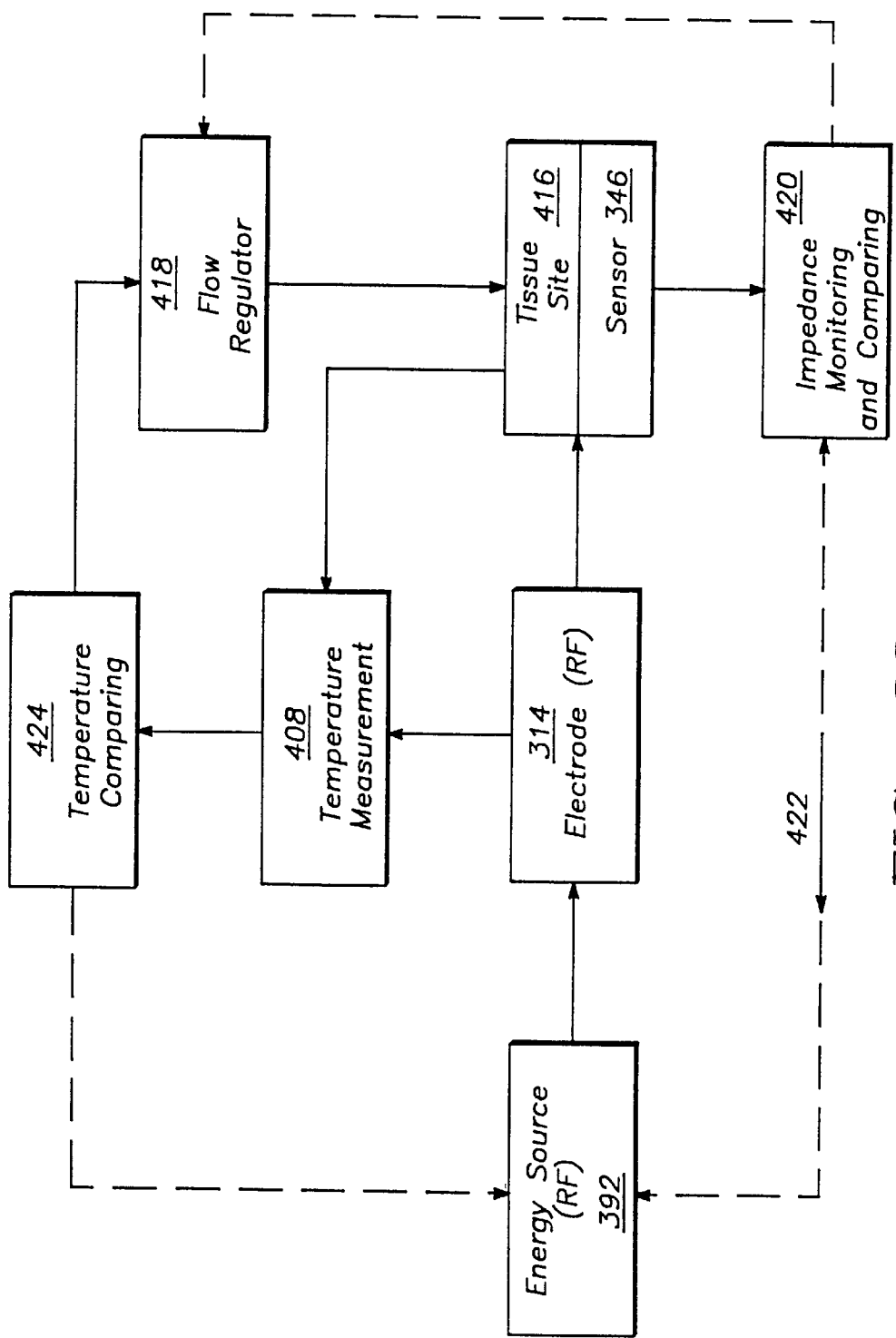
FIG. 23 depicts a block diagram of the operations performed in the feedback control system depicted in FIG. 21.

FIG. 23 illustrates a block diagram of a temperature and impedance feedback system that can be used to control the delivery of energy to tissue site 416 by energy source 392 and the delivery of a cooling medium to electrode 314 and/or tissue site 416 by flow regulator 418. Energy is delivered to RF electrode 314 by energy source 392, and applied to tissue site 416. A monitor 420 ascertains tissue impedance, based on the energy delivered to tissue, and compares the measured impedance value to a set value. If measured impedance is within acceptable limits, energy continues to be applied to the tissue. However if the measured impedance exceeds the set value, a disabling signal 422 is transmitted to energy source 392, ceasing further delivery of energy to RF electrode 314.

The control of the delivery of cooling medium to electrode 314 and/or tissue site 416 is done in the following manner. During the application of energy, temperature measurement device 408 measures the temperature of tissue site 416 and/or RF electrode 314. A comparator 424 receives a signal representative of the measured temperature and compares this value to a pre-set signal representative of the desired temperature. If the measured temperature has not exceeded the desired temperature, comparator 424 sends a signal to flow regulator 418 to maintain the cooling solution flow rate at its existing level. However if the tissue temperature is too high, comparator 424 sends a signal to a flow regulator 418 (connected to an electronically controlled micropump, not shown) representing a need for an increased cooling solution flow rate.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. A sphincter treatment apparatus, comprising:
   an introducer including a distal portion;
   an expandable device including a plurality of arms, each arm of the plurality including a distal section and a proximal section with each of the plurality of arm distal sections being coupled and each of the arm proximal sections being coupled to the introducer distal portion, wherein the expandable device has a sufficient spring force to at least partially dilate a sphincter in a deployed state; and
   an energy delivery device introduceable from the introducer into a selected site of the sphincter, the energy delivery device being configured to deliver sufficient energy to reduce a frequency of relaxation of the sphincter.

2. The apparatus of claim 1, further comprising:
   a sheath at least partially housing the expandable device when the expandable device is in a non-deployed state, the sheath being retractable away from an expandable device distal portion permitting the expandable device to expand to the deployed state.

3. The apparatus of claim 1, wherein the expandable device has a deployed basket configuration.

4. The apparatus of claim 1, wherein the expandable device includes a first arm and a second arm.

5. The apparatus of claim 4, wherein the energy delivery device includes an electrode coupled to the first arm.

6. The apparatus of claim 5, wherein the electrode has a distal portion, the distal portion being coupled to the first arm in a geometric configuration that directs tissue entry of the distal portion at a substantially non-oblique angle relative to a sphincter wall.

7. The apparatus of claim 5, wherein the electrode has a distal portion, the distal portion being coupled to the first arm in a geometric configuration that directs entry of the distal portion at a substantially ninety degree angle relative to a sphincter wall.

8. The apparatus of claim 5, wherein the electrode has a distal portion configured to maintain an entry angle relative to the sphincter wall during introduction of the distal portion into the sphincter.

9. The apparatus of claim 4, wherein a first electrode is introduceable into the sphincter from the first arm and a second electrode is introduceable into the sphincter from the second arm.

10. The apparatus of claim 9, wherein the first electrode is positionable in a lumen of the first arm and the second electrode is positionable in a lumen of the second arm.

11. The apparatus of claim 1, wherein the expandable device includes a first arm, a second arm and a third arm.

12. The apparatus of claim 11, wherein a first electrode is introduceable into the sphincter from the first arm, a second electrode is introduceable into the sphincter from the second arm and a third electrode is introduceable into the sphincter from the third arm.

13. The apparatus of claim 12, wherein the first electrode is positionable in a lumen of the first arm, the second electrode is positionable in a lumen of the second arm and the third electrode is positionable in a lumen of the third arm.

14. The apparatus of claim 1, wherein the expandable device includes a first arm, a second arm, a third arm and a fourth arm.

15. The apparatus of claim 14, wherein a first electrode is introduceable into the sphincter from the first arm, a second electrode is introduceable into the sphincter from the second arm, a third electrode is introduceable into the sphincter from the third arm and a fourth electrode is introduceable into the sphincter from the fourth arm.

16. The apparatus of claim 15, wherein the first electrode is positionable in a lumen of the first arm, the second electrode is positionable in a lumen of the second arm , the third electrode is positionable in a lumen of the third arm and the fourth electrode is positionable in a lumen of the fourth arm.

17. The apparatus of claim 1, wherein each of the plurality of arms have curved geometries.

18. The apparatus of claim 1, wherein the expandable device further includes a supporting strut coupled to the arm.

19. The apparatus of claim 1, wherein at least a portion of the energy delivery device has a distal portion with a geometric configuration that is advanceable into the sphincter with a minimal amount of tearing of a mucosa of the sphincter.

20. The apparatus of claim, 1, wherein at least a portion of the energy delivery device has a distal portion configured to be advanceable into the sphincter while maintaining a constant angle of penetration through a sphincter surface.

21. The apparatus of claim 1, further comprising:
    an advancement member coupled to the energy delivery device.

22. The apparatus of claim 1, further comprising:
    a fluid delivery source coupled to the introducer.

23. The apparatus of claim 1, wherein the energy delivery device includes an RE electrode.

24. The apparatus of claim 23, further comprising:
    an insulation layer in a surrounding relationship to at least a portion of the RE electrode.

25. The apparatus of claim 23, further comprising::
    a sensor coupled to the RF electrode.

26. The apparatus of claim 25, further comprising::
    a feedback control coupled to the sensor.

27. The apparatus of claim 1, wherein the energy delivery device includes a waveguide.

28. The apparatus of claim 27, further comprising:
    a sensor coupled to the waveguide.

29. The apparatus of claim 28, further comprising:
    a feedback control coupled to the sensor.

30. The apparatus of claim 1, wherein the energy delivery device includes a microwave antenna.

31. The apparatus of claim 30, further comprising:
    a sensor coupled to the microwave antenna.

32. The apparatus of claim 31, further comprising:
    a feedback control coupled to the sensor.

33. The apparatus of claim 1, wherein the energy deliver device includes an acoustical transducer.

34. The apparatus of claim 33, further comprising:
    a sensor coupled to the acoustical transducer.

35. The apparatus of claim 34, further comprising:
    a feedback control coupled to the sensor.

36. The apparatus of claim 1, wherein the energy delivery device includes a resistive heating device.

37. The apparatus of claim 36, further comprising:
a sensor coupled to the resistive heating device.

38. The apparatus of claim 37, further comprising:
a feedback control coupled to the sensor.

39. The apparatus of claim 1, further comprising:
a visualization device coupled to the introducer.

40. The apparatus of claim 1, wherein the expandable device is configured to dilate a lower esophageal sphincter.

41. The apparatus of claim 1, wherein the energy delivery device is configured to create a plurality of lesions in the lower esophageal sphincter that reduces a duration of lower esophageal sphincter relaxation.

42. The apparatus of claim 1, wherein the energy delivery device is configured to create a plurality of lesions in the lower esophageal sphincter that reduces a frequency of reflux of stomach contents into an esophagus.

43. The apparatus of claim 1, wherein the energy delivery device is configured to create a plurality of lesions in the lower esophageal sphincter that reduces a frequency of a symptom of reflux of stomach contents into an esophagus.

44. The apparatus of claim 1, wherein the energy delivery device is configured to create a plurality of lesions in the lower esophageal sphincter that reduces an incidence of a sequela of reflux of stomach contents into an esophagus.

45. The apparatus of claim 1, further comprising:
an energy delivery device depth control device coupled to the energy delivery device.

46. A sphincter treatment apparatus, comprising:
an introducer including a distal portion;
an expandable device coupled to the introducer distal portion, the expandable device including a first arm with a proximal section and a distal section and a second arm with a proximal section and a distal section, the first and second arm distal sections being coupled, the expandable device being configured to at least partially dilate a sphincter in a deployed state; and
an energy delivery device coupled to the expandable device, the energy delivery device being configured to deliver sufficient energy to reduce a frequency of relaxation of the sphincter while minimizing cell necrosis of a mucosal layer of the sphincter, at least a portion of the energy delivery device having a distal portion with a geometric configuration that is advanceable into the sphincter with a minimal amount of tearing of a mucosa of the sphincter.

47. The apparatus of claim 46 further comprising:
a sheath at least partially housing the expandable device when the expandable device is in a non-deployed state, the sheath being retractable away from an expandable device distal portion permitting the expandable device to expand to the deployed state.

48. The apparatus of claim 46 wherein the expandable device has a deployed basket configuration.

49. The apparatus of claim 46 wherein the expandable device further comprises:
a third arm.

50. The apparatus of claim 49, wherein the expandable device further comprises:
a fourth arm.

51. The apparatus of claim 50, wherein a first electrode is introduceable into the sphincter from the first arm, a second electrode is introduceable into the sphincter from the second arm and a third electrode is introduceable into the sphincter from the third arm.

52. The apparatus of claim 51, wherein the first electrode is positionable in a lumen of the first arm, the second electrode is positionable in a lumen of the second arm and the third electrode is positionable in a lumen of the third arm.

53. The apparatus of claim 50, wherein a first electrode is introduceable into the sphincter from the first arm, a second electrode is introduceable into the sphincter from the second arm, a third electrode is introduceable into the sphincter from the third arm and a fourth electrode is introduceable into the sphincter from the fourth arm.

54. The apparatus of claim 53, wherein the first electrode is positionable in a lumen of the first arm, the second electrode is positionable in a lumen of the second arm , the third electrode is positionable in a lumen of the third arm and the fourth electrode is positionable in a lumen of the fourth arm.

55. The apparatus of claim 46, wherein the first and second arms have curved geometries.

56. The apparatus of claim 46, wherein the expandable device further includes a supporting strut coupled to the arms.

57. The apparatus of claim 46,
wherein the energy delivery device includes an electrode coupled to the first arm.

58. The apparatus of claim 57, wherein the electrode has a distal portion, the distal portion being coupled to the first arm in a geometric configuration that directs entry of the distal portion at a substantially non-oblique angle relative to a sphincter wall.

59. The apparatus of claim 57, wherein the electrode has a distal portion, the distal portion being coupled to the first arm in a geometric configuration that directs tissue entry of the distal portion at a substantially ninety degree angle relative to a sphincter wall.

60. The apparatus of claim 57, wherein the electrode has a distal portion configured to maintain an entry angle relative to the sphincter wall during introduction of the distal portion into the sphincter.

61. The apparatus of claim 57, wherein a first electrode is introduceable into the sphincter from the first arm and a second electrode is introduceable into the sphincter from the second arm.

62. The apparatus of claim 61, wherein the first electrode is positionable in a lumen of the first arm and the second electrode is positionable in a lumen of the second arm.

63. The apparatus of claim 46, wherein the energy delivery device includes an RE electrode.

64. The apparatus of claim 63, further comprising:
an insulation layer in a surrounding relationship to at least a portion of the RF electrode.

65. The apparatus of claim 63, further comprising:
a sensor coupled to the RE electrode.

66. The apparatus of claim further comprising:
a feedback control coupled to the sensor.

67. The apparatus of claim 46, wherein the expandable device is configured to dilate a lower esophageal sphincter.

68. The apparatus of claim 46, or wherein the energy delivery device is configured to create a plurality of lesions in the lower esophageal sphincter that reduces a duration of lower esophageal sphincter relaxation.

69. The apparatus of claim 46, wherein the energy delivery device is configured to create a plurality of lesions in the lower esophageal sphincter that reduces a frequency of reflux of stomach contents into an esophagus.

70. The apparatus of claim 46, wherein the energy delivery device is configured to create a plurality of lesions in the lower esophageal sphincter that reduces a frequency of a symptom of reflux of stomach contents into an esophagus.

71. The apparatus of claim 46, wherein the energy delivery device is configured to create a plurality of lesions in the lower esophageal sphincter that reduces an incidence of a sequela of reflux of stomach contents into an esophagus.

72. A sphincter treatment apparatus comprising an introducer including a distal portion;

an expandable device coupled to the introducer distal portion, the expandable device including a first arm with a proximal section and a distal section and a second arm with a proximal section and a distal section, the first and second arm distal sections being coupled, the expandable device being configured to at least partially dilate a sphincter in a deployed state; and an energy delivery device coupled to the expandable device, the energy delivery device being configured to deliver sufficient energy to reduce a frequency of relaxation of the sphincter while minimizing cell necrosis of a mucosal layer of the sphincter, at least a portion of the energy delivery device having a distal portion configured to be advanceable into the sphincter while maintaining a constant angle of penetration through a sphincter surface.

73. A sphincter treatment apparatus comprising:

an introducer including a distal portion;

an expandable device coupled to the introducer distal portion, the expandable device including a first arm with a proximal section and a distal section and a second arm with a proximal section and a distal section, the first and second arm distal sections being coupled, the expandable device being configured to at least partially dilate a sphincter in a deployed state;

an energy delivery device coupled to the expandable device, the energy delivery device being configured to deliver sufficient energy to reduce a frequency of relaxation of the sphincter while minimizing cell necrosis of a mucosal layer of the sphincter; and an advancement member coupled to the energy delivery device.

74. A sphincter treatment apparatus comprising:

an introducer including a distal portion;

an expandable device coupled to the introducer distal portion, the expandable device including a first arm with a proximal section and a distal section and a second arm with a proximal section and a distal section, the first and second arm distal sections being coupled, the expandable device being configured to at least partially dilate a sphincter in a deployed state;

an energy delivery device coupled to the expandable device, the energy delivery device being configured to deliver sufficient energy to reduce a frequency of relaxation of the sphincter while minimizing cell necrosis of a mucosal layer of the sphincter; and a fluid delivery source coupled to the introducer.

75. A sphincter treatment apparatus comprising, an introducer including a distal portion;

an expandable device coupled to the introducer distal portion, the expandable device including a first arm with a proximal section and a distal section and a second arm with a proximal section and a distal section, the first and second arm distal sections being coupled, the expandable device being configured to at least partially dilate a sphincter in a deployed state; and an energy delivery device coupled to the expandable device, the energy delivery device including a waveguide means and being configured to deliver sufficient energy to reduce a frequency of relaxation of the sphincter while minimizing cell necrosis of a mucosal layer of the sphincter.

76. The apparatus of claim 25, further comprising:

a sensor coupled to the waveguide.

77. The apparatus of claim 76, further comprising:

a feedback control coupled to the sensor.

78. A sphincter treatment apparatus comprising, an introducer including a distal portion;

an expandable device coupled to the introducer distal portion, the expandable device including a first arm with a proximal section and a distal section and a second arm with a proximal section and a distal section, the first and second arm distal sections being coupled, the expandable device being configured to at least partially dilate a sphincter in a deployed state; and an energy delivery device coupled to the expandable device, the energy delivery device including a microwave antenna and being configured to deliver sufficient energy to reduce a frequency of relaxation of the sphincter while minimizing cell necrosis of a mucosal layer of the sphincter.

79. The apparatus of claim 78, further comprising:

a sensor coupled to the microwave antenna.

80. The apparatus of claim 79, further comprising:

a feedback control coupled to the sensor.

81. A sphincter treatment apparatus comprising, an introducer including a distal portion;

an expandable device coupled to the introducer distal portion, the expandable device including a first arm with a proximal section and a distal section and a second arm with a proximal section and a distal section, the first and second arm distal sections being coupled, the expandable device being configured to at least partially dilate a sphincter in a deployed state; and an energy delivery device coupled to the expandable device, the energy delivery device including an acoustical transducer and being configured to deliver sufficient energy to reduce a frequency of relaxation of the sphincter while minimizing cell necrosis of a mucosal layer of the sphincter.

82. The apparatus of claim 81, further comprising:

a sensor coupled to the acoustical transducer.

83. The apparatus of claim 82, further comprising:

a feedback control coupled to the sensor.

84. A sphincter treatment apparatus comprising, an introducer including a distal portion;

an expandable device coupled to the introducer distal portion, the expandable device including a first arm with a proximal section and a distal section and a second arm with a proximal section and a distal section, the first and second arm distal sections being coupled, the expandable device being configured to at least partially dilate a sphincter in a deployed state; and an energy delivery device coupled to the expandable device, the energy delivery device including a resistive heating device and being configured to deliver sufficient energy to reduce a frequency of relaxation of the sphincter while minimizing cell necrosis of a mucosal layer of the sphincter.

85. The apparatus of claim 84, further comprising:

a sensor coupled to the resistive heating device.

86. The apparatus of claim 85, further comprising:

a feedback control coupled to the sensor.

87. A sphincter treatment apparatus comprising:

an introducer including a distal portion;

an expandable device coupled to the introducer distal portion, the expandable device including a first arm with a proximal section and a distal section and a second arm with a proximal section and a distal section, the first and second arm distal sections being coupled, the expandable device being configured to at least partially dilate a sphincter in a deployed state;

an energy delivery device coupled to the expandable device, the energy delivery device being configured to deliver sufficient energy to reduce a frequency of relaxation of the sphincter while minimizing cell necrosis of a mucosal layer of the sphincter; and a visualization device coupled to the introducer.

88. A sphincter treatment apparatus comprising:

an introducer including a distal portion;

an expandable device coupled to the introducer distal portion, the expandable device including a first arm with a proximal section and a distal section and a second arm with a proximal section and a distal section, the first and second arm distal sections being coupled, the expandable device being configured to at least partially dilate a sphincter in a deployed state;

an energy delivery device coupled to the expandable device, the energy delivery device being configured to deliver sufficient energy to reduce a frequency of relaxation of the sphincter while minimizing cell necrosis of a mucosal layer of the sphincter; and an energy delivery device depth control device coupled to the energy delivery device.

89. A sphincter treatment apparatus, comprising:

an introducer including a distal portion;

an expandable device including a plurality of arms, each arm of the plurality including a distal section and a proximal section with each of the plurality of arms distal sections being coupled and each of the arms proximal sections being coupled to the introducer distal portion, the expandable device including a first arm, a second arm and a third arm, wherein the expandable device is configured to at least partially dilate a sphincter in a deployed state; and a first electrode introduceable into the sphincter from the first arm, a second electrode introduceable into the sphincter from the second arm and a third electrode introduceable into the sphincter from the third arm, the first, second and third electrodes being configured to be coupled to a power source.

90. The apparatus of claim 89, wherein the first electrode is positionable in a lumen of the first arm, the second electrode is positionable in a lumen of the second arm and the third electrode is positionable in a lumen of the third arm.

* * * * *

UNITED STATES PATENT AND TRADEMARK OFFICE
CERTIFICATE OF CORRECTION

PATENT NO. : 6,749,607 B2
APPLICATION NO. : 09/971085
DATED : June 15, 2004
INVENTOR(S) : Edwards et al.

It is certified that error appears in the above-identified patent and that said Letters Patent is hereby corrected as shown below:

Column 14, line 39, delete "RE" and substitute -- RF -- .

Column 14, line 42, delete "RE" and substitute -- RF -- .

Column 15, line 46, after "46" insert -- ,72, 73 or 74, --.

Column 15, line 52, after "46" insert -- ,72, 73 or 74, --.

Column 15, line 54, after "46" insert -- ,72, 73 or 74, --.

Column 16, line 15, after "46," insert -- 72, 73 or 74, --.

Column 16, line 17, after "46," insert -- 72, 73 or 74, --.

Column 16, line 20, after "46," insert -- 72, 73 or 74, --.

Column 16, line 44, after "46," insert -- 72 , 73 or 74, --.

Column 16, line 45, delete "RE" and substitute -- RF -- .

Column 16, line 50, delete "RE" and substitute -- RF -- .

Column 16, line 51, after "claim" insert -- 65, -- .

Column 16, line 53, after "46," insert -- 72, 73, or 74, -- .

Column 16, line 55, after "or" insert -- 72, 73, or 74, -- .

Column 16, line 59, after "46," insert -- 72, 73, or 74, --.

Column 16, line 63, after "46," insert -- 72, 73, or 74, -- .

Column 16, line 67, after "46," insert -- 72, 73, or 74, -- .

UNITED STATES PATENT AND TRADEMARK OFFICE
CERTIFICATE OF CORRECTION

PATENT NO.        : 6,749,607 B2
APPLICATION NO. : 09/971085
DATED             : June 15, 2004
INVENTOR(S)       : Edwards et al.

It is certified that error appears in the above-identified patent and that said Letters Patent is hereby corrected as shown below:

Column 18, line 3, after "claim" delete "25" and substitute -- 75 --.

Signed and Sealed this

Fourth Day of December, 2007

JON W. DUDAS
*Director of the United States Patent and Trademark Office*